(12) United States Patent
Sverdlove et al.

(10) Patent No.: US 10,813,852 B2
(45) Date of Patent: Oct. 27, 2020

(54) BI-PHASE MICELLAR LIQUID PRODUCT COMPRISING CERAMIDES

(71) Applicant: L'OREAL, Paris (FR)

(72) Inventors: Madeline Jane Sverdlove, Jersey City, NJ (US); Patricia Maribel Brieva, Manalapan, NJ (US); Miao Wang, Westfield, NJ (US); Maggie Helen Su, Cranford, NJ (US)

(73) Assignee: L'OREAL, Paris (FR)

( * ) Notice: Subject to any disclaimer, the term of this patent is extended or adjusted under 35 U.S.C. 154(b) by 112 days.

(21) Appl. No.: 15/814,628

(22) Filed: Nov. 16, 2017

(65) Prior Publication Data

US 2019/0142706 A1     May 16, 2019

(51) Int. Cl.

| | |
|---|---|
| *A61K 8/03* | (2006.01) |
| *A61K 8/31* | (2006.01) |
| *A61K 8/58* | (2006.01) |
| *A61K 8/42* | (2006.01) |
| *A61K 8/63* | (2006.01) |
| *A61K 8/41* | (2006.01) |
| *A61K 8/06* | (2006.01) |
| *A61Q 19/00* | (2006.01) |
| *A61Q 1/14* | (2006.01) |
| *A61K 8/34* | (2006.01) |
| *A61Q 19/10* | (2006.01) |
| *A61K 8/68* | (2006.01) |
| *A61K 8/39* | (2006.01) |

(52) U.S. Cl.
CPC .......... *A61K 8/03* (2013.01); *A61K 8/06* (2013.01); *A61K 8/31* (2013.01); *A61K 8/34* (2013.01); *A61K 8/345* (2013.01); *A61K 8/39* (2013.01); *A61K 8/41* (2013.01); *A61K 8/416* (2013.01); *A61K 8/42* (2013.01); *A61K 8/585* (2013.01); *A61K 8/63* (2013.01); *A61K 8/68* (2013.01); *A61Q 1/14* (2013.01); *A61Q 19/007* (2013.01); *A61Q 19/10* (2013.01)

(58) Field of Classification Search
CPC . A61K 8/03; A61K 8/31; A61K 8/585; A61K 8/42; A61K 8/63; A61K 8/41; A61K 8/345; A61K 8/416; A61K 8/34; A61K 8/06; A61Q 19/10; A61Q 19/007; A61Q 1/14
See application file for complete search history.

(56) References Cited

U.S. PATENT DOCUMENTS

| | | | |
|---|---|---|---|
| 6,709,663 B2 | 3/2004 | Espinoza | |
| 2010/0055220 A1* | 3/2010 | Akatsuka | A61K 8/06 424/776 |
| 2011/0177144 A1* | 7/2011 | Tashiro | A61K 8/06 424/401 |
| 2013/0035395 A1* | 2/2013 | Tashiro | A61K 8/06 514/625 |
| 2016/0235685 A1 | 8/2016 | Greaves et al. | |

OTHER PUBLICATIONS

Madison, Kathi C., "Barrier Function of the Skin: 'La Raison d'Etre' of the Epidermis," The Journal of Investigative Dermatology, vol. 121, No. 2, Aug. 2003, pp. 231-241.
Coderch, Luisa et al., "Ceramides and Skin Function," American Journal of Clinical Dermatology, vol. 4, No. 2, 2003, pp. 107-129.
Rawlings, Anthony V. et al., "Stratum Corneum Moisturization at the Molecular Level: an update in relation to the dry skin cycle," The Journal of Investigative Dermatology, vol. 124, 2005, pp. 1099-1110.

\* cited by examiner

*Primary Examiner* — Robert S Cabral
(74) *Attorney, Agent, or Firm* — Polsinelli PC

(57) ABSTRACT

The present disclosure relates to bi-phase micellar liquid products that include ceramides and other components that are beneficial to the skin. In particular, the products include: (a) a fatty phase comprising one or more fatty compounds and one or more silicones; and (b) an aqueous phase comprising one or more ceramides, one or more water-soluble solvents, one or more surfactants, and water. The products are particularly unique because the ceramides are solubilized in the aqueous phase of the products. In addition to being useful for cleansing the skin, the products support natural lipid barrier function of the skin and improve skin hydration.

25 Claims, No Drawings

BI-PHASE MICELLAR LIQUID PRODUCT COMPRISING CERAMIDES

FIELD OF THE DISCLOSURE

The present disclosure relates to bi-phase micellar liquid products that include ceramides and other components that are beneficial to the skin. The product is particularly unique because the ceramides are solubilized in the aqueous phase of the products. In addition to being useful for cleansing the skin, the products support natural lipid barrier function of the skin and improve skin hydration.

BACKGROUND

Skin acts as a natural barrier between internal and external environments and therefore plays an important role in vital biological functions such as protection against mechanical and chemical injury, micro-organisms, and ultraviolet damage. The health and appearance of skin, however, can deteriorate due to environmental factors, genetic makeup, nutrition, and sun exposure. With aging, the outer skin layer (epidermis) thins, even though the number of cell layers remains unchanged. The number of pigment-containing cells (melanocytes), however, decreases. Therefore, the skin appears pale and translucent. Large pigmented spots (age spots, liver spots, or lentigos) may appear in sun-exposed areas. Changes in the connective tissue reduce the skin's strength and elasticity. This is known as elastosis. It is more noticeable in sun-exposed areas (solar elastosis). Elastosis produces the leathery, weather-beaten appearance common to farmers, sailors, and others who spend a large amount of time outdoors. Dehydration increases the risk of skin injury. Poor nutrition can also negatively impact the skin, causing dryness, rash, and puffiness.

Ceramides are a group of natural waxy, fatty substances in the skin, composed of sphingosine and lipids (fatty acids) bonded together. Ceramides make up about 50% of all skin lipids and are manufactured in the lower, living cells of the epidermis. As the cells mature and move to the surface, ceramides are released to the topmost layer, the stratum corneum. In the stratum corneum layer, ceramides combine with cholesterol (another important lipid found in the skin) and fatty acids to form an ordered, tightly-packed, layered, sheet-like arrangement between the dead cells. Ceramides and cholesterol protect against moisture loss to keep skin youthful and supple, and support the skin's matrix, keeping it firm. Young individuals manufacture ample ceramides and cholesterol to keep the skin healthy. However, with age, production declines, and skin begins to sag and wrinkle.

SUMMARY OF THE DISCLOSURE

The present disclosure relates to bi-phase micellar liquid products that may be used for cleansing, hydrating, and strengthening the skin. As the name implies, bi-phase products provide two phases—an aqueous phase and a fatty phase. When the two phases are shaken together, the water phase and fatty phase temporarily mix to create a mixed product. During use, the fatty phase dissolves oily materials (including waterproof makeup) whilst the aqueous phase washes or carries the oily materials away. Therefore, the product can be used as a facial wash, makeup remover, and moisturizer all in one.

The bi-phase micellar liquid products are unique because the one or more ceramides are present in the aqueous phase of the product. Ceramides are a family of waxy sphingolipids that are not typically soluble in water. Therefore, ceramides have typically been solubilized in fatty carries that are incorporated into permanent and stable emulsions. The inventors of the instant case proceeded differently. Instead of including the ceramides in a fatty phase, the ceramides are incorporated into the aqueous phase. The ceramides are suspended in the aqueous phase with micelles (tiny balls of cleansing oil molecules) throughout the aqueous phase. These micelles are attracted to dirt, oil, makeup, etc., and are therefore able to draw out impurities from the skin without drying out the skin.

The aqueous phase and the fatty phase of the bi-phase micellar liquid products do not combine to form a permanent and stable emulsion. Rather, upon shaking or mixing, the aqueous phase and the fatty phase temporarily combine to form an unstable mixture that is briefly emulsified or partially emulsified. Shortly after mixing, for example, within about 5 to about 30 minutes, the aqueous phase and the fatty phase begin to noticeably phase separate.

In some instances, the bi-phase micellar liquid products also include cholesterol and/or phytosphingosine. Like the one or more ceramides, the cholesterol and/or phytosphingosine are also uniquely included in the aqueous phase with micelles. Again, this is contrary to what is typical in the art. Although the aqueous phase incorporates components such as ceramides, cholesterol, and phytosphingosine (components that are not soluble in water), the aqueous phase is typically transparent. Additionally, the fatty phase of the bi-phase micellar liquid product is also typically transparent. When the aqueous phase and the fatty phase are temporarily mixed, however, the mixture becomes opaque (cloudy). Nonetheless, the transparent nature of the fatty phase and the aqueous phase is restored upon phase separation of the two phases.

A bi-phase micellar liquid product according to the instant disclosure typically includes: (a) a fatty phase, the fatty phase comprising: one or more fatty compounds and one or more silicones; and (b) an aqueous phase, the aqueous phase comprising: one or more ceramides, one or more water-soluble solvents, one or more surfactants, and water. The aqueous phase may also include cholesterol and/or phytosphingosine; and may even further include thickening agents, preservatives, pH adjusting agents and/or buffering agents, salts, etc.

The one or more surfactants may be anionic, cationic, nonionic, and/or amphoteric (zwitterionic) surfactants. Nonetheless, in many instances the bi-phase micellar liquid products includes at least one or more nonionic surfactants. Non-limiting examples of nonionic surfactants include polyglycerol esters, alkylpolyglucosides, alkyl(ether)phosphates, fatty acid alkanolamides, and a mixture thereof. Furthermore, in some cases, one or more of the nonionic surfactants has an HLB (hydrophile-lipophile balance) of at least 12, at least 13, or at least 14 to 20.

Non-limiting examples of fatty compounds include oils, waxes, alkanes, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, ceramide, and a mixture thereof.

Non-limiting examples of silicones include polyorganosiloxanes, polyalkylsiloxanes, polyarylsiloxanes, polyalkarylsiloxanes, polyestersiloxanes, and a mixture thereof. More specific non-limiting examples include dimethicone, cyclomethicone (cyclopentasiloxane), amodimethicone, trimethyl silyl amodimethicone, phenyl trimethicone, trimethyl siloxy silicate, and a mixture thereof.

Non-limiting examples of ceramides include ceramide-EOS, ceramide-NS, ceramide-NP, ceramide-EOH, ceramide-AS, ceramide-NH, ceramide-AP, ceramide-AH, Ceramide-OS, ceramide-OH, and a mixture thereof.

Non-limiting examples of water-soluble solvents include glycerin, $C_{1-4}$ alcohols, organic solvents, polyols, glycols, and a mixture thereof.

The bi-phase micellar liquid products may also include one or more preservatives, which are usually included in the aqueous phase. Non-limiting examples of preservatives include parahydroxybenzoic acid esters (also known as parabens, for example, methyl paraben, ethyl paraben, propyl paraben), phenoxyethanol, imidazolidinyl urea, diazolidinyl urea, chlorhexidine digluconate, sodium benzoate, caprylyl glycol, iodopropynyl butyl carbamate, pentylene glycol, alkyl trimethylammonium bromides (such as myrtrimonium bromide), dodecyl-trimethylammonium bromide, hexadecyltrimethylammonium bromide, and a mixture thereof.

The bi-phase micellar liquid products are useful for treating the skin, in particular the skin of the face. The products can be used as a facial wash, makeup remover, and/or a moisturizer, as the products are particularly effective at cleansing, hydrating, and strengthening the skin. Accordingly, the instant disclosure relates to methods for cleansing the skin, methods for hydrating the skin, methods for removing makeup from the skin, methods of strengthening the barrier properties of the skin, etc. The methods generally include shaking or mixing the bi-phase micellar product and applying the mixture to the skin. For example, the hands and/or a cotton ball or pad (or other device, for example, a cloth, a tissue, a wipe, etc.) may be used to apply the mixture to the skin. A cotton ball or pad (or other device) can also be used to absorb and remove dirt, grease, unwanted makeup, etc. from the skin.

DETAILED DESCRIPTION OF THE DISCLOSURE

The instant disclosure is directed to unique bi-phase micellar liquid products and methods of using the products. A bi-phase liquid product is a product that includes two distinct liquid phases. In the instant case, one phase is an aqueous phase and the other phase is a fatty phase. When the bi-phase micellar liquid product of the instant case remains at rest, the two phases will separate, but when the product is shaken or vigorously stirred, the two phases mix to form a temporary or partial emulsion. An example of a temporary emulsion is vinaigrette. Oil and vinegar are combined in a jar. When the jar is mixed, the oil and vinegar come together for a short time, but after remaining at rest for a period of time, the oil and vinegar separate from one another. Mayonnaise, on the other hand, is an example of a permanent emulsion, consisting of egg yolks and oil.

More specifically, in the context of the instant disclosure, the term "bi-phase micellar liquid product" relates to a product having two separate phases, an aqueous phase and a fatty phase, which temporarily emulsify (or partially emulsify) by shaking, but undergo phase separation after the shaking is stopped. Products of this type are referred to as "bi-phase products" or "two-phase products." They differ from emulsions in that when at rest, the two phases are separate instead of being emulsified one in the other. The two phases are separated at rest by a single interface, whereas, in emulsions, one of the phases is dispersed in the other in the form of a multitude of droplets, and therefore have multiple interfaces, these multiple interfaces generally being stabilized with emulsifying surfactants and/or emulsifying polymers.

The use of bi-phase liquid products necessitates shaking in order to form an extemporaneous emulsion (or partial emulsion). This emulsion must be of sufficient quality and stability to enable homogeneous application of the two phases, but such that when at rest, the two phases become separated and regain their initial state, this phenomenon being commonly known as "phase separation." Phase separation (or demixing) of the two phases after use is one of the desired qualities of liquid bi-phase products.

As the term indicates, a "bi-phase micellar liquid product" is liquid and therefore the term relates to the liquid components of a final commercial product, for example, a consumer product, which in addition to the bi-phase micellar liquid product includes packaging to contain or house the bi-phase micellar liquid product. In other words, a consumer product includes, for example, a container (e.g., a bottle, jar, tube, etc.) containing the bi-phase micellar liquid product. Therefore, a weight percentage based on the total weight of the bi-phase micellar liquid product would be different than a weight percentage based on the total weight of a consumer product containing the bi-phase micellar liquid product because the weight of the container would need to be taken into account. The instant disclosure relates to bi-phase micellar liquid products and to final products (e.g., consumer products) containing the bi-phase micellar liquid products.

With respect to the bi-phase micellar liquid products of the instant disclosure, components such as ceramides, cholesterol, and phytosphingosine are uniquely present in the aqueous phase. These components are incorporated into the aqueous phase as part of a "micellar system" (a type of microemulsion).

A "micelle" is an aggregate or supramolecular assembly of surfactant molecules dispersed in a liquid (an aqueous phase in the instant case). Micellar systems are a special class of dispersions or microemulsions that are typically transparent or translucent. The ceramides, cholesterol, and phytosphingoine are incorporated into the micellar systems and dispersed throughout the aqueous phase. Thus, a "bi-phase micellar liquid product" according to the instant disclosure is a two-phase liquid product (an aqueous phase and a fatty phase), wherein the aqueous phase comprises dispersed micelles that carry the ceramides, cholesterol, and phytosphingosine.

The bi-phase micellar liquid products of the instant disclosure typically include: (a) a fatty phase, the fatty phase comprising: one or more fatty compounds and one or more silicones; and (b) an aqueous phase comprising: one or more ceramides, optionally cholesterol and/or phytosphingosine, one or more water-soluble solvents, one or more surfactants, and water. In some instances, the aqueous phase also includes one more additional components such as one or more thickening agents, one or more preservatives, one or more pH adjusting agents and/or buffering agents, one or more salts, etc.

The aqueous phase of the bi-phase micellar liquid product is typically the predominant phase, i.e., the product comprises a greater amount of the aqueous phase than the fatty phase. For example, the product may include from about 1 to about 49 wt. % of the fatty phase and from about 51 to about 99 wt. % of the aqueous phase, based on the total weight of the product. In some cases, the product comprises from about 5 to about 40 wt. % of the fatty phase and about 60 to about 95 wt. % of the aqueous phase. Additionally, the product may include from about 5 to about 30 wt. % of the fatty phase and about 70 to about 95 wt. % of the aqueous phase; or from about 10 to about 30 wt. % of the fatty phase and about 70 to about 90 wt. % of the aqueous phase. Even further, the product may include about 10 to about 30 wt. % of the fatty phase and about 70 to about 90 wt. % of the aqueous phase; or about 10 to about 25 wt. % of the fatty phase and about 75 to about 90 wt. % of the aqueous phase.

Non-limiting examples of fatty compounds include oils, waxes, alkanes, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof.

The total amount of the one or more fatty compounds can vary but is typically about 1 to about 35 wt. %, based on the total weight of the bi-phase micellar liquid product. In some instances, the total amount of the one or more fatty compounds is from about 1 to about 30 wt. %, about 1 to about 25 wt. %, about 1 to about 20 wt. %, about 1 to about 15 wt. %, about 1 to about 10 wt. %, about 2 to about 35 wt. %, about 2 to about 30 wt. %, about 2 to about 25 wt. %, about 2 to about 20 wt. %, about 2 to about 15 wt. %, about 2 to about 10 wt. %, about 5 to about 35 wt. %, about 5 to about 30 wt. %, about 5 to about 25 wt. %, about 5 to about 20 wt. %, about 5 to about 15 wt. %, or about 5 to about 10 wt. %.

Non-limiting examples of silicones include polyorganosiloxanes, polyalkylsiloxanes, polyarylsiloxanes, polyalkarylsiloxanes, polyestersiloxanes, and a mixture thereof. More specific non-limiting examples include dimethicone, cyclomethicone (cyclopentasiloxane), amodimethicone, trimethyl silyl amodimethicone, phenyl trimethicone, trimethyl siloxy silicate, and a mixture thereof. In some instances, the bi-phase micellar liquid product includes dimethicone, cyclomethicone (cyclopentasiloxane), amodimethicone, or a mixture thereof. Furthermore, in some cases, cyclomethicone (cyclopentasiloxane) is particularly useful. A more exhaustive list of useful silicones that may be included in the bi-phase micellar liquid product is provided later, under the heading "Silicones."

The total amount of the one or more silicones can vary but is typically about 1 to about 40 wt. %, based on the total weight of the bi-phase micellar liquid product. In some instances, the total amount of the one or more fatty compounds is from about 1 to about 35 wt. %, about 1 to about 30 wt. %, about 1 to about 25 wt. %, about 1 to about 20 wt. %, about 1 to about 15 wt. %, about 1 to about 10 wt. %, about 2 to about 35 wt. %, about 2 to about 30 wt. %, about 2 to about 25 wt. %, about 2 to about 20 wt. %, about 2 to about 15 wt. %, about 2 to about 10 wt. %, about 5 to about 35 wt. %, about 5 to about 30 wt. %, about 5 to about 25 wt. %, about 5 to about 20 wt. %, about 5 to about 15 wt. %, or about 5 to about 10 wt. %.

Ceramides are a family of waxy sphingolipids containing mainly sphingosine, phytosphingosine or 6-hydroxysphingosine, C18-sphingoid bases in amide linkage with a variety of nonhydroxy, α-hydroxy, or ω-hydroxy acids. These differences in type and extent of hydroxylation, together with the N-acyl chain lengths and the presence of an additional acylation at the ω-side of the N-acyl group, account for the heterogeneity of the epidermal sphingolipids. Ceramides make up about 50% of all skin lipids and are manufactured in the lower, living cells of the epidermis.

Various ceramides are known by different names. For example, ceramide-EOS has been referred to as ceramide-1. A non-limiting group of ceramides are listed below along with their chemical structures.

Ceramide 1

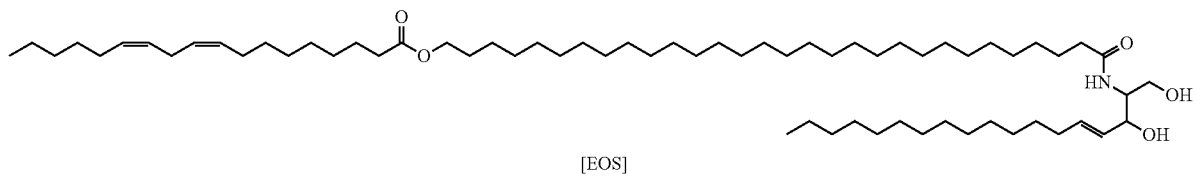

[EOS]

Ceramide 2

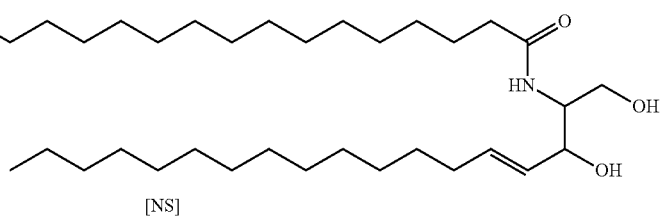

[NS]

Ceramide 3

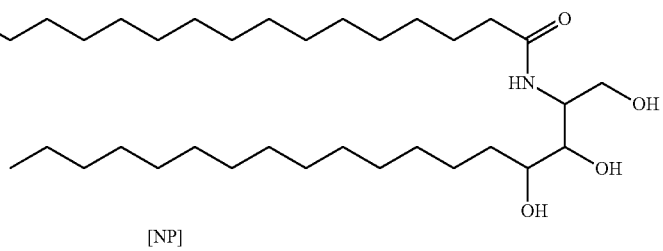

[NP]

Ceramide 4
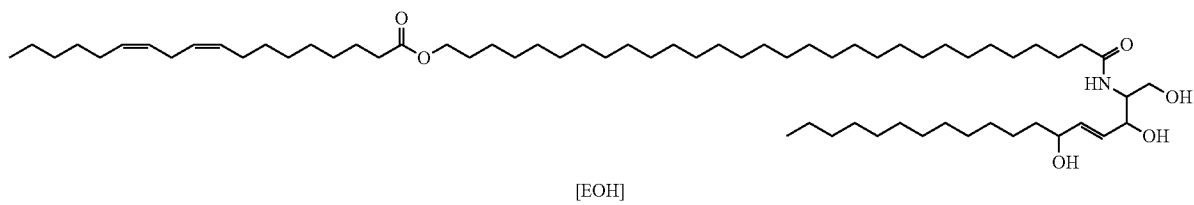
[EOH]
Ceramide 5
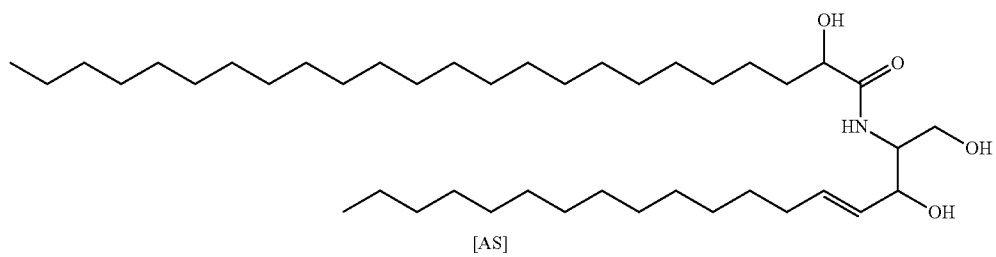
[AS]
Ceramide 6
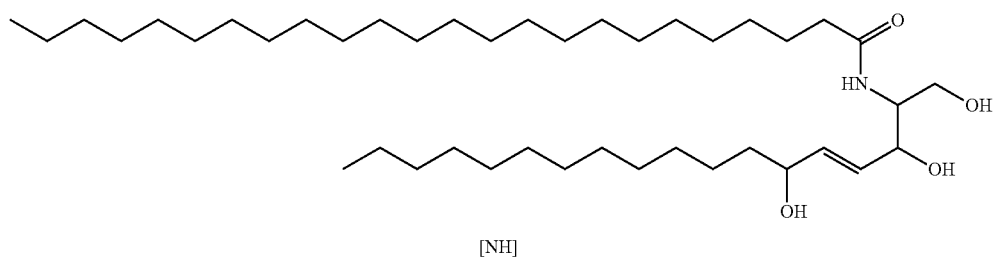
[NH]
Ceramide 7
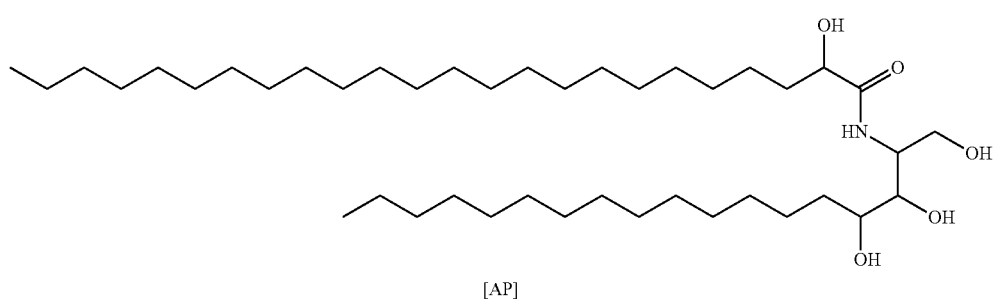
[AP]
Ceramide 8
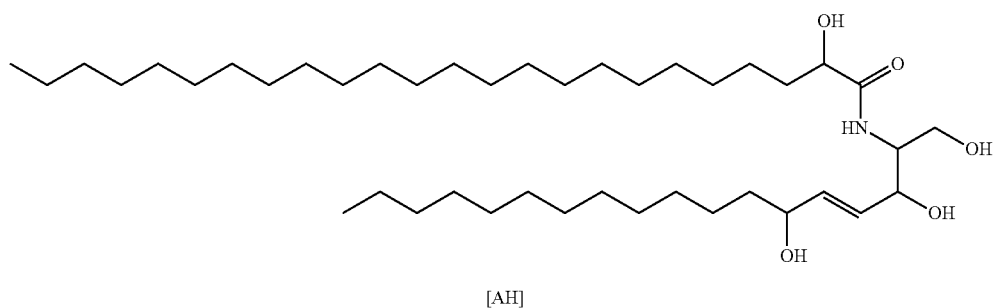
[AH]
Ceramide 9
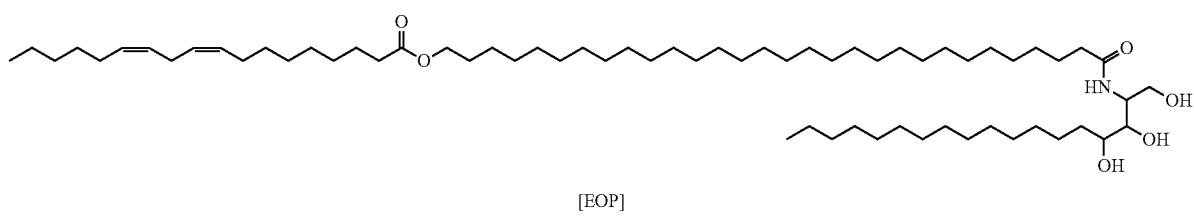
[EOP]

The aqueous phase of the bi-phase micellar liquid product includes one or more ceramides. In some cases, the aqueous phase of the bi-phase micellar liquid products includes multiple ceramides, for example, two or more ceramides, three or more ceramides, four or more ceramides, etc. For example, the aqueous phase may include a combination of ceramides such as a combination of ceramide EOP, ceramide NP, and ceramide AP. Any combination of ceramides may be included, especially any combination of the ceramides depicted above.

The total amount of the one or more ceramides in the bi-phase micellar liquid product may vary but is typically in an amount greater than zero to about 5 wt. %, based on the total weight of the bi-phase micellar liquid product. In some cases the total amount of the one or more ceramides is an amount greater than zero to about 4 wt. %, in an amount greater than zero to about 3 wt. %, in an amount greater than zero to about 2 wt. %, in an amount greater than zero to about 1 wt. %, in an amount greater than zero to about 0.5 wt. %, in an amount greater than zero to about 0.1 wt. %, or in an amount greater than zero to about 0.05 wt. %, based on the total weight of the bi-phase micellar liquid product.

The bi-phase micellar liquid product may include cholesterol. Cholesterol is a lipid naturally found in human skin oil; it has a water-binding capacity and is important in repairing normal skin barrier function. The cholesterol may be included in either the fatty phase or the aqueous phase of the bi-phase micellar liquid product (or in both phases). Nonetheless, the micellar system of the bi-phase micellar liquid product allows the cholesterol to be uniquely incorporated into the aqueous phase. Thus, in some cases it is preferable to include the cholesterol in the aqueous phase.

The total amount of cholesterol in the bi-phase micellar liquid product may vary but is typically in an amount greater than zero to about 5 wt. %, based on the total weight of the bi-phase micellar liquid product. Likewise, the total amount of cholesterol may be in an amount greater than zero to about 4 wt. %, in an amount greater than zero to about 3 wt. %, in an amount greater than zero to about 2 wt. %, in an amount greater than zero to about 1 wt. %, in an amount greater than zero to about 0.5 wt. %, in an amount greater than zero to about 0.1 wt. %, or in an amount greater than zero to about 0.05 wt. %, based on the total weight of the bi-phase micellar liquid product.

The bi-phase micellar liquid product may include phytosphingosine, a compound that is important for maintaining healthy skin. Phytosphingosine helps prevent loss of moisture from the skin, regulate epidermal cell growth, differentiation, and apoptosis, and it possesses bactericidal and anti-inflammatory properties. The phytosphingosine may be included in either the fatty phase or the aqueous phase of the bi-phase micellar liquid product (or in both phases). Nonetheless, the micellar system of the bi-phase micellar liquid product allows the phytosphingosine to be uniquely incorporated into the aqueous phase. Thus, in some cases it is preferable to include the phytosphingosine in the aqueous phase.

The total amount of phytosphingosine in the bi-phase micellar liquid product may vary but is typically in an amount greater than zero to about 5 wt. %, based on the total weight of the bi-phase micellar liquid product. Likewise, the total amount of phytosphingosine may be in an amount greater than zero to about 4 wt. %, in an amount greater than zero to about 3 wt. %, in an amount greater than zero to about 2 wt. %, in an amount greater than zero to about 1 wt. %, in an amount greater than zero to about 0.5 wt. %, in an amount greater than zero to about 0.1 wt. %, or in an amount greater than zero to about 0.05 wt. %, based on the total weight of the bi-phase micellar liquid product.

In one embodiment, the bi-phase micellar liquid product includes one or more ceramides, cholesterol, and phytosphingosine. The one or more ceramides, cholesterol, and phytosphingosine may all be incorporated into the aqueous phase of the product. For example, the aqueous phase of the bi-phase micellar liquid product may include a combination of ceramides (such as ceramide EOP, ceramide NP, and ceramide AP), cholesterol, and phytosphingosine. The total amount of the one or more ceramides, cholesterol, and phytosphingosine in the bi-phase micellar liquid product may vary but is typically in an amount greater than zero to about 5 wt. %, based on the total weight of the bi-phase micellar liquid product. Furthermore, the total amount of the one or more ceramides, cholesterol, and phytosphingosine may be in an amount greater than zero to about 4 wt. %, in an amount greater than zero to about 3 wt. %, in an amount greater than zero to about 2 wt. %, in an amount greater than zero to about 1 wt. %, in an amount greater than zero to about 0.5 wt. %, in an amount greater than zero to about 0.1 wt. %, or in an amount greater than zero to about 0.05 wt. %, based on the total weight of the bi-phase micellar liquid product.

The aqueous phase of the bi-phase micellar liquid product typically includes one or more water-soluble solvents. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvent has a solubility of at least 60%, 70%, 80%, or 90%. Non-limiting examples of water-soluble solvents include, for example, glycerin, $C_{1-4}$ alcohols, organic solvents, fatty alcohols, fatty ethers, fatty esters, polyols, glycols, and a mixture thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-di methyl-2,4-pentanediol, 2,5-dimethyl-2,5-hexanediol, 5-hexene-1,2-diol, and 2-ethyl-1,3-hexanediol, and a mixture thereof.

In some instances, the one or more water-soluble solvents are selected from the group consisting of glycerin, $C_{1-4}$ alcohols, organic solvents, polyols, glycols, and a mixture thereof.

The one or more surfactants of the bi-phase micellar liquid products may be anionic, cationic, nonionic, and/or amphoteric (zwitterionic) surfactants. The total amount of the one or more surfactants may vary but is typically about 0.01 to about 8 wt. %, based on the total weight of the bi-phase micellar liquid product. Furthermore, the total amount of the one or more surfactants may be about 0.01 to about 6 wt. %, about 0.01 to about 5 wt. %, about 0.01 to about 4 wt. %, about 0.01 to about 2 wt. %, about 0.05 to about 8 wt. %, about 0.05 to about 6 wt. %, about 0.05 to about 5 wt. %, about 0.05 to about 4 wt. %, about 0.05 to about 2 wt. %, about 0.1 to about 8 wt. %, about 0.1 to about 6 wt. %, about 0.1 to about 5 wt. %, about 0.1 to about 4 wt. %, or about 0.1 to about 2 wt. %, based on the total weight of the bi-phase micellar liquid product.

In some cases the bi-phase micellar liquid products include at least one or more nonionic surfactants. Non-limiting examples of nonionic surfactants include polyglycerol esters, alkylpolyglucosides, alkyl(ether)phosphates, fatty acid alkanolamides, and a mixture thereof. Furthermore, one or more of the nonionic surfactants may have an HLB (hydrophilic-lipophilic balance) of at least 12 to 20, at least 13 to 20, at least 14 to 20, or at least 15 to 20.

The amphiphilic character of small-size surfactants can be characterized by the HLB. The HLB concept is the best-known method to select a surfactant suitable for an application. This semiempirical method assigns a surfactant a HLB number according to its chemical structure. Several experimental and numeric methods have been developed over the years to determine HLB numbers. These methods, initially developed for nonionic surfactants, are mainly based on the respective sizes of the hydrophobic and hydrophilic moieties of the surfactant molecules.

Many nonionic surfactants are known and may be useful. Non-limiting classes of nonionic surfactants include esters of polyols with fatty acids and alkoxylated derivatives thereof, alkylpolyglucosides, sucrose esters, alkoxylated ethers of fatty acids and glucose or alkylglucose, esters of fatty acids and glucose or alkylglucose, sorbitol esters of fatty acids and alkoxylated derivatives thereof, alkoxylated fatty alcohols (for example, ethoxylated fatty alcohols), alkanolamides, polyglylcerol esters, and a mixture thereof. In some cases, one or more nonionic surfactants may be selected from the group consisting of polyglycerol esters, alkylpolyglucosides, alkyl(ether)phosphates, fatty acid alkanolamides, and a mixture thereof. Additionally, one or more polyglycerol esters and/or one or more alkylpolyglucosides may be particularly useful. For example, the product may include polyglyceryl-4 captrate and decyl gucoside.

Non-limiting polyglycerol esters include those of the following formula:

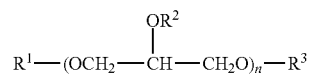

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Examples include glyceryl monomyristate, glyceryl monopalmitate, glyceryl monostearate, glyceryl isostearate, glyceryl monooleate, glyceryl ester of mono(olive oil fatty acid), glyceryl dioleate and glyceryl distearate. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

Alkyl polyglucosides that may be used include compounds of the following formula:

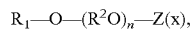

wherein,
$R^1$ is an alkyl group having 8-18 carbon atoms;
$R^2$ is an ethylene or propylene group;
Z is a saccharide group with 5 to 6 carbon atoms;
n is an integer from 0 to 10; and
x is an integer from 1 to 5.

Such alkyl polyglucoside compounds include lauryl glucoside, octyl glucoside, decyl glucoside, coco glucoside, sucrose laurate, caprylyl/capryl glucoside, and sodium lauryl glucose carboxylate, and mixtures thereof. In some cases, at least one alkyl poly glucoside compound is selected from the group consisting of lauryl glucoside, decyl glucoside, coco glucoside, and a mixture thereof.

Non-limiting examples of alkyl(ether)phosphates include, alkoxylated alkyl phosphate esters and alkyl phosphate esters corresponding to a mono-ester of the following formula and/or a salt thereof:

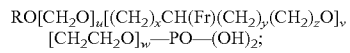

a di-ester corresponding to the following formula and/or a salt thereof:

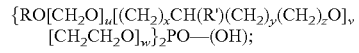

a tri-ester of the following formula and/or a salt thereof:

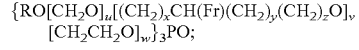

and combinations thereof, wherein:
R is a hydrocarbon radical containing from 6 to 40 carbon atoms;

u, v and w, independently of one another, represent numbers of from 0 to 60;

x, y and z, independently of one another, represent numbers of from 0 to 13;

R' represents hydrogen, alkyl, the sum of x+y+z being ?0. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

Furthermore, in the above three formula, R may be linear or branched, acyclic or cyclic, saturated or unsaturated, aliphatic or aromatic, substituted or unsubstituted, preferably a linear or branched, acyclic $C_{6-40}$ alkyl or alkenyl group or a $C_{1-40}$ alkyl phenyl group, more particularly a $C_{8-22}$ alkyl or alkenyl group or a $C_{4-18}$ alkyl phenyl group, more preferably a $C_{12-18}$ alkyl group or alkenyl group or a $C_{6-16}$ alkyl phenyl group; u, v, w, independently of one another, is preferably a number from 2 to 20, more preferably a number from 3 to 17 and most preferably a number from 5 to 15;

x, y, z, independently of one another, are preferably a number from 2 to 13, more preferably a number from 1 to 10 and most preferably a number from 0 to 8.

More specific, non-limiting examples of alkyl(ether)phosphates include PPG-5-ceteth-10 phosphate, oleth-3 phosphate, oleth-10 phosphate, ceteth-10 phosphate, dicetyl phosphate, cetyl phosphate, and stearyl phosphate.

Non-limiting examples of fatty alkanolamides (fatty acid alkanolamides) t include cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, and a mixture thereof.

In some embodiments, the bi-phase micellar liquid product comprises one or more nonionic surfactants selected from the group consisting of polyglycerol esters, alkylpolyglucosides, and a mixture thereof. In some case, one or more polyglycerol esters and one or more alkylpolyglucosides are included in the bi-phase micellar liquid product. For example, the bi-phase micellar liquid product may include polyglyceryl-4 caprate and/or decyl glucoside. A more exhaustive list of nonionic surfactants that may be included in the hair-treatment compositions is provided later, under the heading "Nonionic Surfactants."

The total amount of the one or more nonionic surfactants may vary but is typically about 0.01 to about 8 wt. %, based on the total weight of the bi-phase micellar liquid product. Furthermore, the total amount of the one or more nonionic surfactants may be about 0.01 to about 6 wt. %, about 0.01 to about 5 wt. %, about 0.01 to about 4 wt. %, about 0.01 to about 2 wt. %, about 0.05 to about 8 wt. %, about 0.05 to about 6 wt. %, about 0.05 to about 5 wt. %, about 0.05 to about 4 wt. %, about 0.05 to about 2 wt. %, about 0.1 to about 8 wt. %, about 0.1 to about 6 wt. %, about 0.1 to about 5 wt. %, about 0.1 to about 4 wt. %, or about 0.1 to about 2 wt. %, based on the total weight of the bi-phase micellar liquid product.

The bi-phase micellar liquid products may also include one or more preservatives, which are usually included in the aqueous phase. Non-limiting examples of preservatives include parahydroxybenzoic acid esters (also known as parabens, for example, methyl paraben, ethyl paraben, propyl paraben), phenoxyethanol, imidazolidinyl urea, diazolidinyl urea, chlorhexidine digluconate, sodium benzoate, caprylyl glycol, iodopropynyl butyl carbamate, pentylene glycol, alkyl trimethylammonium bromides (such as myrtrimonium bromide), dodecyl-trimethylammonium bromide, hexadecyltrimethylammonium bromide, and a mixture thereof. Particularly useful preservatives include myrtrimonium bromide, phenoxyethanol, and a mixture thereof.

The total amount of the one or more preservatives may vary but is typically about 0.01 to about 5 wt. %, based on the total weight of the bi-phase micellar liquid product. Furthermore, the total amount of the one or more preservatives may be about 0.01 to about 4 wt. %, about 0.01 to about 2 wt. %, about 0.01 to about 1 wt. %, about 0.05 to about 5 wt. %, about 0.05 to about 4 wt. %, about 0.05 to about 2 wt. %, about 0.05 to about 1 wt. %, about 0.1 to about 5 wt. %, about 0.1 to about 4 wt. %, about 0.1 to about 4 wt. %, about 0.1 to about 2 wt. %, or about 0.1 to about 1 wt. %, based on the total weight of the bi-phase micellar liquid product.

The bi-phase micellar liquid product may contain one or more thickening agent (also referred to as thickeners or viscosity modifying agents). Classes of such agents include, but are not limited to, viscous liquids, such as polyethylene glycol, semisynthetic polymers, such as semisynthetic cellulose derivatives, synthetic polymers, such as carbomers, poloxamers, and acrylates/beheneth-25 methacrylate copolymer, acrylates copolymer, polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, starches, such as hydroxypropyl starch phosphate, potato starch (modified or unmodified), celluloses such as hydroxyethylcellulose, guars such as hydroxypropyl guar, and a mixture thereof. In some instances, the thickening agent may be carrageenan, acacia, tragacanth, alginates (e.g., sodium alginate), xanthan gum, or a mixture thereof. A more exhaustive list of useful thickening agents that may be included in the bi-phase micellar liquid product is provided later, under the heading "Thickening Agents."

If one or more thickening agents is included in the bi-phase micellar liquid product, the total amount of thickening agent is typically fairly low, e.g., below 1 wt. %. For example, the total amount of the one or more thickening agent may in an amount greater than zero to about 1 wt. %, in an amount greater than zero to about 0.5 wt. %, in an amount greater than zero to about 0.1 wt. %, or in an amount greater than zero to about 0.05 wt. %.

The total amount of water in the bi-phase micellar liquid product may vary but is typically about 60 to about 90 wt. %, based on the total weight of the bi-phase micellar liquid product. Furthermore, the total amount of water may be about 60 to about 85 wt. %, about 60 to about 80 wt. %, about 65 to about 90 wt. %, about 65 to about 85 wt. %, about 65 to about 80 wt. %, about 70 to about 90 wt. %, about 70 to about 85 wt. %, or about 70 to about 80 wt. %, based on the total weight of the bi-phase micellar liquid product.

As noted previously, the aqueous phase of the bi-phase micellar liquid product includes micelles that carry the ceramides, cholesterol, and phytosphingosine. Nonetheless, it is possible that the fatty phase also include ceramides, cholesterol, and/or phytosphingosine. In other words, the components of the micelles in the aqueous phase are not precluded from existing in the fatty phase (or from existing outside of the micelles). Nonetheless, the components of the micelles (e.g., ceramides, cholesterol, and/or phytosphingosine) are typically primarily in the aqueous phase, as part of the micelles. For example, at least 50% of the ceramides, cholesterol, and/or phytosphingosine of the bi-phase micellar liquid product re typically in the aqueous phase, in the form of micelles. Furthermore, in some cases, at least 60%, at least 70%, at least 80%, about 90%, about 95%, at least 98%, at least 99% of the ceramides, cholesterol, and/or phytosphingosine are in the aqueous phase of the bi-phase micellar liquid product in the form of micelles. Furthermore, the fatty phase may be free or essentially free of ceramides, cholesterol, and/or phytosphingosine.

In one embodiment, the instant disclosure relates to a bi-phase micellar liquid product comprising:
(a) about 5 to about 40 wt. %, about 5 to about 30 wt. %, or about 5 to about 25 wt. % of a fatty phase, the fatty phase comprising:
  one or more fatty compounds, for example, one or more fatty compounds including one or more volatile hydrocarbon oils having from 8 to 16 carbon atoms and their mixtures and in particular branched $C_8$ to $C_{16}$ alkanes such as $C_8$ to $C_{16}$ isoalkanes (also known as isoparaff ins), e.g., isododecane, isodecane, isohexadecane;
  one or more silicones, for example, one or more silicones selected from the group consisting of polyorganosiloxanes, polyalkylsiloxanes, polyarylsiloxanes, polyalkarylsiloxanes, polyestersiloxanes, and a mixture thereof; and
(b) about 60 to about 95 wt. %, about 60 to about 90 wt. %, or about 60 to about 85 wt. % of an aqueous phase, the aqueous phase comprising:
  one or more ceramides;
  optionally, cholesterol;
  optionally, phytoshingosine;
  one or more water-soluble solvents, for example, one or more water-soluble solvents selected from the group consisting of glycerin, $C_{1-4}$ alcohols, organic solvents, polyols, glycols, and a mixture thereof;
  one or more surfactants, in particular, one or more nonionic surfactants selected from the group consisting of polyglycerol esters, alkylpolyglucosides, alkyl(ether)phosphates, fatty acid alkanolamides, and a mixture thereof; and
  water.

Both the fatty phase and the aqueous phase of the bi-phase micellar liquid product may be transparent when separated from the other phase. The bi-phase micellar liquid product in the above embodiment may include two or more ceramides or three or more ceramides, for example, it may include a combination of ceramide EOP, ceramide NP, and ceramide AP. The total amount of ceramides may be in an amount greater than zero to about 0.5 wt. %, based on the total weight of the bi-phase micellar liquid product. In some cases the total amount of the ceramides is an amount greater than zero to about 0.1 wt. % or an amount greater than zero to about 0.05 wt. %, based on the total weight of the bi-phase micellar liquid product.

In some instances, the bi-phase micellar liquid product includes both cholesterol and phytosphingosine. The total amount of cholesterol in the bi-phase micellar liquid product may be an amount greater than zero to about 0.5 wt. %, based on the total weight of the bi-phase micellar liquid product. Furthermore, the total amount of cholesterol may be an amount greater than zero to about 0.1 wt. % or an amount greater than zero to about 0.05 wt. %, based on the total weight of the bi-phase micellar liquid product. Likewise, the total amount of phytosphingosine in the bi-phase micellar liquid product may be an amount greater than zero to about 0.5 wt. %, based on the total weight of the bi-phase micellar liquid product. Furthermore, the total amount of phytosphingosine may be an amount greater than zero to about 0.1 wt. % or an amount greater than zero to about 0.05 wt. %, based on the total weight of the bi-phase micellar liquid product.

In some instances, the bi-phase micellar liquid product includes a combination of ceramides (for example, a combination of ceramide EOP, ceramide NP, and ceramide AP), cholesterol, and phytosphingosine. The total amount of all ceramides, cholesterol, and phytosphingosine in the bi-phase micellar liquid product may be an amount greater than zero to about 1 wt. %, based on the total weight of the bi-phase micellar liquid product. In some cases the total amount of all ceramides, cholesterol, and phytosphingosine in the bi-phase micellar liquid product may be an amount greater than zero to about 0.5 wt. %, or an amount greater than zero to about 0.1 wt. %, based on the total weight of the bi-phase micellar liquid product.

The bi-phase micellar liquid product may further include one or more preservatives, for example, one or more preservatives selected from the group consisting parahydroxybenzoic acid esters (also known as Parabens, for example, methyl paraben, ethyl paraben, propyl paraben), phenoxyethanol, imidazolidinyl urea, diazolidinyl urea, chlorhexidine digluconate, sodium benzoate, caprylyl glycol, iodopropynyl butyl carbamate, pentylene glycol, alkyl trimethylammonium bromides (such as myrtrimonium bromide), dodecyl-trimethylammonium bromide, hexadecyltrimethylammonium bromide, and a mixture thereof. In some cases, the bi-phase micellar liquid product includes myrtrimobium bromide, phenoxyethanol, or a mixture thereof. The total amount of the one or more preservatives may vary but may be about 0.01 to about 5 wt. %, about 0.01 to about 4 wt. %, about 0.01 to about 2 wt. %, or about 0.01 to about 1 wt. %, based on the total weight of the bi-phase micellar liquid product.

In one embodiment, the instant disclosure relates to a bi-phase micellar liquid product comprising:
(a) about 5 to about 40 wt. %, about 5 to about 30 wt. %, or about 5 to about 25 wt. % of a fatty phase, the fatty phase comprising:
  about 1 to about 25 wt. %, about 1 to about 20 wt. %, or about 5 to about 15 wt. % of one or more fatty compounds, for example, at least one or more alkanes, such as isodecane, isododecane, isooctane, dodecane, isohexadecane, and a mixture thereof;
  about 1 to about 25 wt. %, about 1 to about 20 wt. %, or about 5 to about 25 wt. % of one or more silicones, for example, one or more silicones selected from the group consisting of dimethicone, cyclomethicone (cyclopentasiloxane), amodimethicone, trimethyl silyl amodimethicone, phenyl trimethicone, trimethyl siloxy silicate, and a mixture thereof; and
(b) about 60 to about 95 wt. %, about 60 to about 90 wt. %, or about 60 to about 85 wt. % of an aqueous phase, the aqueous phase comprising:
  one or more ceramides in an amount greater than zero to about 1 wt. %, to about 0.5 wt. %, or to about 0.1 wt. %, wherein the one or ceramides are selected from the group consisting of ceramide-EOS, ceramide-NS, ceramide-NP, ceramide-EOH, ceramide-AS, ceramide-NH, ceramide-AP, ceramide-AH, Ceramide-OS, ceramide-OH, and a mixture thereof.

cholesterol in an amount greater than zero to about 1 wt. %, to about 0.5 wt. %, or to about 0.1 wt. %;

phytoshingosine in an amount greater than zero to about 1 wt. %, to about 0.5 wt. %, or to about 0.1 wt. %;

about 0.1 to about 25 wt. %, about 1 to about 20 wt. %, or about 1 to about 15 wt. % of one or more water-soluble solvents, for example, one or more water-soluble solvents selected from the group consisting of glycerin, $C_{1-4}$ alcohols, organic solvents, polyols, glycols, and a mixture thereof;

about 0.01 to about 10 wt. %, about 0.05 to about 6 wt. %, or about 0.1 to about 5 wt. % of one or more surfactants, in particular, one or more nonionic surfactants selected from the group consisting of polyglycerol esters, alkylpolyglucosides, alkyl (ether)phosphates, fatty acid alkanolamides, and a mixture thereof; and water.

Both the fatty phase and the aqueous phase of the bi-phase micellar liquid product may be transparent when separated from the other phase.

The bi-phase micellar liquid product in the above embodiment may include two or more ceramides or three or more ceramides, for example, it may include a combination of ceramide EOP, ceramide NP, and ceramide AP. The total amount of all ceramides, cholesterol, and phytosphingosine in the bi-phase micellar liquid product may be an amount greater than zero to about 1 wt. %, based on the total weight of the bi-phase micellar liquid product. In some cases the total amount of all ceramides, cholesterol, and phytosphingosine in the bi-phase micellar liquid product may be an amount greater than zero to about 0.5 wt. %, or an amount greater than zero to about 0.1 wt. %, based on the total weight of the bi-phase micellar liquid product.

The bi-phase micellar liquid product may further include one or more preservatives, for example, one or more preservatives selected from the group consisting parahydroxybenzoic acid esters (also known as Parabens, for example, methyl paraben, ethyl paraben, propyl paraben), phenoxyethanol, imidazolidinyl urea, diazolidinyl urea, chlorhexidine digluconate, sodium benzoate, caprylyl glycol, iodopropynyl butyl carbamate, pentylene glycol, alkyl trimethylammonium bromides (such as myrtrimonium bromide), dodecyl-trimethylammonium bromide, hexadecyltrimethylammonium bromide, and a mixture thereof. In some cases, the bi-phase micellar liquid product includes myrtrimobium bromide, phenoxyethanol, or a mixture thereof. The total amount of the one or more preservatives may vary but may be about 0.01 to about 5 wt. %, about 0.01 to about 4 wt. %, about 0.01 to about 2 wt. %, or about 0.01 to about 1 wt. %, based on the total weight of the bi-phase micellar liquid product.

In one embodiment, the instant disclosure relates to a bi-phase micellar liquid product comprising:
(a) about 5 to about 40 wt. %, about 5 to about 30 wt. %, or about 5 to about 25 wt. % of a fatty phase, the fatty phase comprising:
 about 1 to about 25 wt. %, about 1 to about 20 wt. %, or about 5 to about 15 wt. % of one or more fatty compounds, for example, at least one or more alkanes, such as isodecane, isododecane, isooctane, dodecane, isohexadecane, and a mixture thereof, and in particular, isohexadecane;
 about 1 to about 25 wt. %, about 1 to about 20 wt. %, or about 5 to about 25 wt. % of one or more silicones, for example, one or more silicones selected from the group consisting of di methicone, cyclomethicone (cyclopentasiloxane), amodimethicone, trimethyl silyl amodimethicone, phenyl trimethicone, trimethyl siloxy silicate, and a mixture thereof, and in particular, cyclomethicocne (cyclopentasiloxane); and (b) about 60 to about 95 wt. %, about 60 to about 90 wt. %, or about 60 to about 85 wt. % of an aqueous phase, the aqueous phase comprising:
 a combination of ceramide EOP, ceramide NP, and ceramide AP in an amount greater than zero to about 1 wt. %, to about 0.5 wt. %, or to about 0.1 wt. %;
 cholesterol in an amount greater than zero to about 1 wt. %, to about 0.5 wt. %, or to about 0.1 wt. %;
 phytoshingosine in an amount greater than zero to about 1 wt. %, to about 0.5 wt. %, or to about 0.1 wt. %;
 about 0.1 to about 25 wt. %, about 1 to about 20 wt. %, or about 1 to about 15 wt. % of one or more water-soluble solvents, for example, one or more water-soluble solvents selected from the group consisting of glycerin, $C_{1-4}$ alcohols, organic solvents, polyols, glycols, and a mixture thereof;
 about 0.01 to about 10 wt. %, about 0.05 to about 6 wt. %, or about 0.1 to about 5 wt. % of one or more surfactants, in particular, one or more nonionic surfactants selected from the group consisting of polyglycerol esters, alkylpolyglucosides, and a mixture thereof, for example, a nonionic surfactant selected from the group consisting of decyl glucoside, polyglyceryl-4 caprate, and a mixture thereof;
 one or more preservatives; and
 about 60 to about 90 wt. %, about 65 to about 85 wt. %, or about 70 to about 80 wt. % of water.

Both the fatty phase and the aqueous phase of the bi-phase micellar liquid product may be transparent when separated from the other phase.

The one or more preservatives may be selected from the group consisting parahydroxybenzoic acid esters (also known as Parabens, for example, methyl paraben, ethyl paraben, propyl paraben), phenoxyethanol, imidazolidinyl urea, diazolidinyl urea, chlorhexidine digluconate, sodium benzoate, caprylyl glycol, iodopropynyl butyl carbamate, pentylene glycol, alkyl trimethylammonium bromides (such as myrtrimonium bromide), dodecyl-trimethylammonium bromide, hexadecyltrimethylammonium bromide, and a mixture thereof. In some cases, the bi-phase micellar liquid product includes myrtrimobium bromide, phenoxyethanol, or a mixture thereof. The total amount of the one or more preservatives may vary but may be about 0.01 to about 5 wt. %, about 0.01 to about 4 wt. %, about 0.01 to about 2 wt. %, or about 0.01 to about 1 wt. %, based on the total weight of the bi-phase micellar liquid product.

The bi-phase micellar liquid products are useful for treating the skin, in particular the skin of the face. The products can be used as a facial wash, makeup remover, and/or a moisturizer, as the products are particularly effective at cleansing, hydrating, and strengthening the skin. Accordingly, the instant disclosure relates to methods for cleansing the skin, methods for hydrating the skin, methods for removing makeup from the skin, methods of strengthening the barrier properties of the skin, etc. The methods generally include shaking or mixing the bi-phase micellar product and applying the mixture to the skin. For example, the hands and/or a cotton ball or pad (or other device, for example, a cloth, a tissue, a wipe, etc.) may be used to apply the mixture to the skin. A cotton ball or pad (or other device) can also be used to absorb and remove dirt, grease, unwanted makeup, etc. from the skin.

In one embodiment, the instant disclosure relates to a method for cleansing the skin comprising applying the bi-phase micellar liquid product to the skin and removing at least a portion of the product from the skin. In another embodiment, the instant disclosure relates to a method for hydrating the skin comprising applying the bi-phase micellar liquid product to the skin and removing at least a portion of the product from the skin. In another embodiment, the instant disclosure relates to a method for removing makeup from the skin comprising applying the bi-phase micellar liquid product to skin upon which makeup has been applied and removing at least a portion of the makeup from the skin. In yet another embodiment, the instant disclosure relates to a method for supporting natural lipid barrier function of skin comprising applying the bi-phase micellar liquid product to the skin. The methods may include shaking or mixing the bi-phase micellar liquid product shortly before applying the product to the skin, e.g., shaking or mixing the product within about 1, 5, or 10 minutes of applying the product to the skin.

More exhaustive but non-limiting lists of components useful in the bi-phase micellar liquid products of the instant disclosure are provided below.

Silicones

Exemplary silicones include, without limitation, cyclic silicones, such as those having 3 to 6, or 3 to 4 or 3 to 5, (or any of 3, 4, 5, or 6) Si—O groups in the cyclic backbone chain (e.g., siloxanes). In some cases, the cyclic silicone is a volatile silicone. In some cases, the cyclic silicone is a low viscosity silicone. Exemplary cyclic silicones include, without limitation, cyclomethicone, cyclotetrasiloxane, cyclopentasiloxane (e.g., Cyclomethicone 5-NF), cyclohexasiloxane and a mixture of cyclohexasiloxane and cyclopenasiloxane (e.g., DOW CORNING 246 Fluid (d6+d5)). Other non-limiting examples of silicones are silicones having side groups or side chains. In some cases, the side groups are hydrophobic. In some cases, the side groups are straight chained, while in other embodiments the side groups are branched. Exemplary side chains include those having 1 to 6, or 2 to 6, or 3 to 6 or 3 to 6 or 5 to 6 carbons or heteroatoms (e.g., O, S, or N) (or any combination thereof). Exemplary linear side chains include, without limitation, methyl, ethyl, propyl, butyl, pentyl, and hexyl. Exemplary branched side chains include, without limitation, isopropyl, isobutyl, and tert-butyl. In one nonlimiting embodiment, the branched side chain is —O—Si(CH$_3$)$_3$. Nonlimiting examples of silicones having branched side chains are stearyl dimethicone and phyenyltrimethicone, cetyl dimethicone, caprylyl methicone, PEG/PPG 18/18 dimethicone the structures of which are as follows:

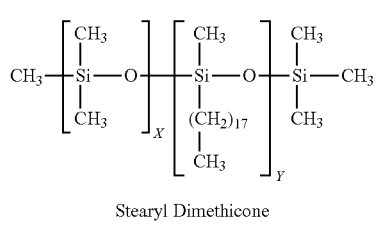

Stearyl Dimethicone

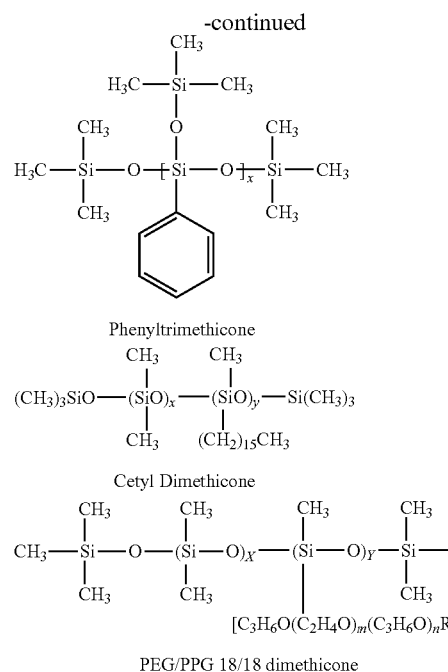

Phenyltrimethicone

Cetyl Dimethicone

PEG/PPG 18/18 dimethicone

In the above formulas m, n, x, and y may independently be integers of 1 to 100, 1 to 80, 1 to 60, 1 to 50, 1 to 40, 1 to 30, 1 to 20, or 1 to 10. In some cases, the side chains are cyclic. Cyclic side chains include aliphatic side chains and aromatic side chains. A nonlimiting example of a cyclic side chain is phenyl.

With regard to silicones having hydrophilic or polar groups, as described previously, silicones that are repulsive with regard to the hydrophobic chains of the oil are thought to produce more stable foams because they do not inhibit the hydrophobic-hydrophobic interactions of the oil. Exemplary hydrophilic or polar groups include oxygen-containing groups, such as carbonyl groups, hydroxy groups, ether, ester, carboxylic groups, which replace one or more methyl groups. The hydrophilic/polar groups are present alternatively in the main chain of the silicone or in a side chain. Nonlimiting examples of a silicone having a hydrophilic group are PEG/PPG 18/18 dimethicone and dimethiconol, the structures of which are:

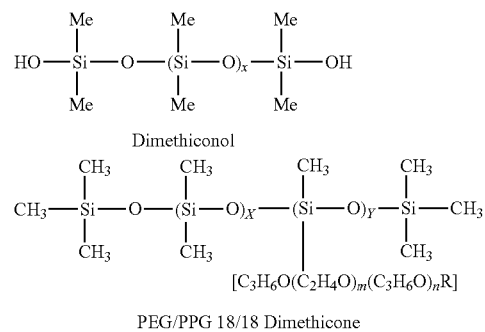

Dimethiconol

PEG/PPG 18/18 Dimethicone

X, y, m, and n are as defined above, and R is a $C_1$ to $C_{10}$ alkyl.

Another type of specific non limiting volatile silicone is a volatile short chain linear alkylmethylsilicone fluid. The volatile short chain linear alkylmethylsilicone fluid has the formula:

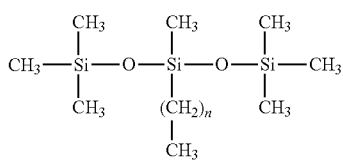

In the above formula, the integer represented by n has a value of five to twelve. Preferably, n has a value of five to eight. Compounds include, for example, 3-hexyl-1,1,1,3,5,5,5-heptamethyltrisiloxane and 3-octyl-1,1,1,3,5,5,5-heptamethyltrisiloxane.

Yet another type of volatile silicone in accordance with the present invention is a volatile short chain linear phenylmethylsilicone fluid. The volatile short chain linear phenylmethylsilicone fluid has the formula:

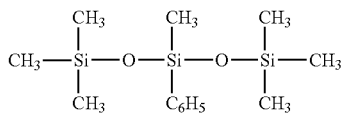

This compound is 3-phenyl-1,1,1,3,4,4,4-heptamethyltrisiloxane. Further volatile silicone fluids useful in the compositions described herein include, without limitation, are decamethylcyclopentasiloxane (DMCPS) which has a molecular weight of about 370, a refractive index of 1.40, and the formula $[(Me_2)SiO]_5$; the compound 3-hexyl-1,1,1,3,5,5,5-heptamethyltrisiloxane (HHMTS) which has a molecular weight of about 306, and a refractive index of 1.41; and the compound 3-phenyl-1,1,1,3,5,5,5-heptamethyltrisiloxane (PHMTS) which has a molecular weight of about 298 and a refractive index of 1.45.

As amino silicone that may be used in the scope of the instant disclosure, the following can be cited:

a) polysiloxanes corresponding to formula (A):

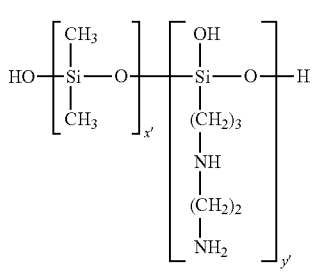

in which x' and y' are integers such that the weight-average molecular weight (Mw) is comprised between about 5000 and 500 000 b) amino silicones corresponding to formula (B):

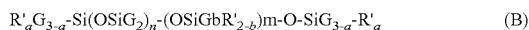

in which:
G, which may be identical or different, designate a hydrogen atom, or a phenyl, OH or $C_1$-$C_8$ alkyl group, for example methyl, or $C_1$-$C_8$ alkoxy, for example methoxy,
a, which may be identical or different, denote the number 0 or an integer from 1 to 3, in particular 0;
b denotes 0 or 1, and in particular 1;
m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;
R', which may be identical or different, denote a monovalent radical having formula —$C_qH_{2q}L$ in which q is a number ranging from 2 to 8 and L is an optionally quaternized amino group chosen from the following groups:
—NR"-Q-N(R")$_2$
N(R")$_2$
N+(R")$_3$ A−
N+H(R")$_2$ A−
N+H$_2$(R") A−
N(R")-Q-N+R"H$_2$ A−
NR"-Q-N+(R")$_2$H A−
NR"-Q-N+(R")$_3$ A−,
in which R", which may be identical or different, denote hydrogen, phenyl, benzyl, or a saturated monovalent hydrocarbon-based radical, for example a $C_1$-$C_{20}$ alkyl radical; Q denotes a linear or branched $C_rH_{2r}$ group, r being an integer ranging from 2 to 6, preferably from 2 to 4; and A− represents a cosmetically acceptable ion, in particular a halide such as fluoride, chloride, bromide or iodide.

A group of amino silicones corresponding to this definition (B) is represented by the silicones called "trimethylsilylamodimethicone" having formula (C):

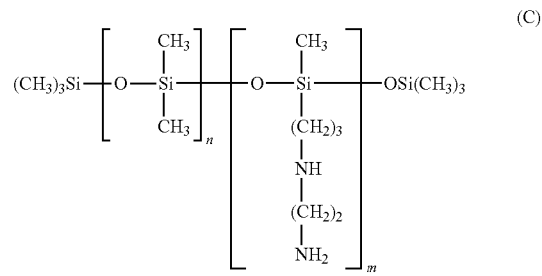

in which n and m have the meanings given above, in formula B.

Another group of amino silicones corresponding to this definition is represented by silicones having the following formulae (D) or (E):

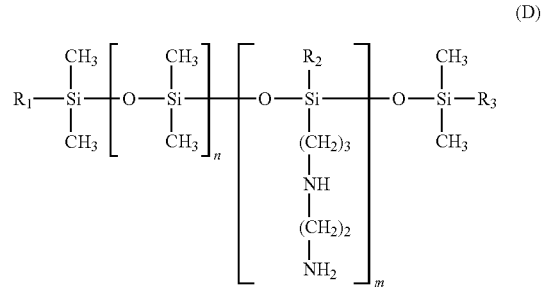

in which:
m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5;

$R_1$, $R_2$, $R_3$, which may be identical or different, represent a hydroxy or $C_1$-$C_4$ alkoxy radical, where at least one of the radicals $R_1$ to $R_3$ denotes an alkoxy radical.

The alkoxy radical is preferably a methoxy radical.

The hydroxy/alkoxy mole ratio ranges preferably from 0.2:1 to 0.4:1 and preferably from 0.25:1 to 0.35:1 and more particularly equals 0.3:1.

The weight-average molecular weight (Mw) of the silicone ranges preferably from 2000 to 1 000 000, more particularly from 3500 to 200 000.

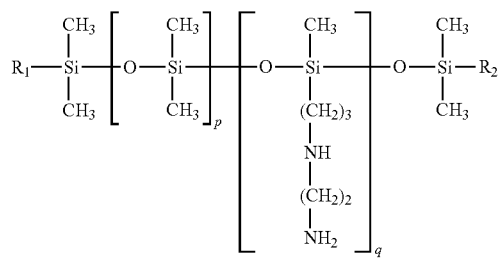

(E)

in which:

p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;

$R_1$, $R_2$, which are different, represent a hydroxy or $C_1$-$C_4$ alkoxy radical, where at least one of the radicals $R_1$ or $R_2$ denotes an alkoxy radical.

The alkoxy radical is preferably a methoxy radical.

The hydroxy/alkoxy mole ratio ranges generally from 1:0.8 to 1:1.1 and preferably from 1:0.9 to 1:1 and more particularly equals 1:0.95.

The weight-average molecular weight (Mw) of the silicone ranges preferably from 2000 to 200 000, even more particularly 5000 to 100 000 and more particularly from 10 000 to 50 000.

Commercial products corresponding to these silicones having structure (D) or (E) may include in their composition one or more other amino silicones whose structure is different than formulae (D) or (E).

A product containing amino silicones having structure (D) is sold by Wacker under the name Belsil® ADM 652.

A product containing amino silicones having structure (E) is sold by Wacker under the name Fluid WR 1300®.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The number-average size of the silicone particles in the emulsion generally ranges from 3 nm to 500 nanometres. Preferably, in particular as amino silicones having formula (E), microemulsions are used whose average particle size ranges from 5 nm to 60 nanometres (limits included) and more preferably from 10 nm to 50 nanometres (limits included). Accordingly, according to the invention the microemulsions of amino silicone having formula (E) sold as Finish CT 96 E® or SLM 28020® by Wacker can be used.

Another group of amino silicones corresponding to this definition is represented by the following formula (F):

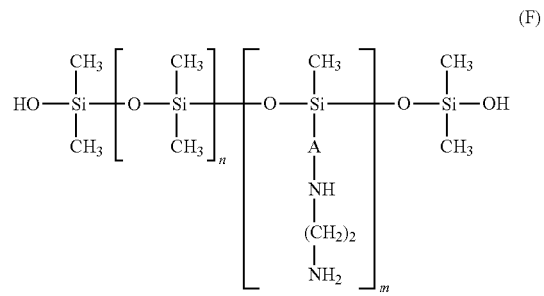

(F)

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably linear.

The weight-average molecular weight (Mw) of these amino silicones ranges preferably from 2000 to 1 000 000 and even more particularly from 3500 to 200 000.

A preferred silicone of formula (F) is amodimethicone (INCI name) sold under the tradename XIAMETER® MEM-8299 Cationic Emulsion by Dow Corning.

Another group of amino silicones corresponding to this definition is represented by the following formula (G):

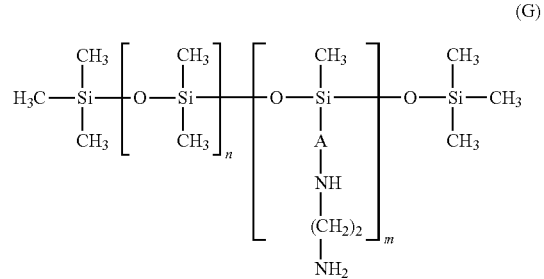

(G)

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably branched.

The weight-average molecular weight (Mw) of these amino silicones ranges preferably from 500 to 1 000 000 and even more particularly from 1000 to 200 000.

A silicone having this formula is for example DC2-8566 Amino Fluid by Dow Corning.

c) amino silicones corresponding to formula (H):

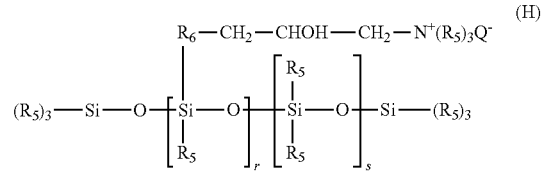

(H)

in which:
- $R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;
- $R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;
- Q– is an anion such as a halide ion, in particular chloride, or an organic acid salt (for example acetate);
- r represents a mean statistical value from 2 to 20 and in particular from 2 to 8;
- s represents a mean statistical value from 20 to 200 and in particular from 20 to 50.

Such amino silicones are described more particularly in patent U.S. Pat. No. 4,185,087.

d) quaternary ammonium silicones having formula (I):

$$R_8-\underset{\underset{R_7}{|}}{\overset{\overset{R_7}{|}}{N^+}}-CH_2-\underset{}{\overset{\overset{OH}{|}}{CH}}-CH_2-R_6-\left[\underset{\underset{R_7}{|}}{\overset{\overset{R_7}{|}}{Si}}-O\right]_r\underset{\underset{R_7}{|}}{\overset{\overset{R_7}{|}}{Si}}-R_6-CH_2-CHOH-CH_2-\underset{\underset{R_7}{|}}{\overset{\overset{R_7}{|}}{N^+}}-R_8 \quad 2X^- \quad (I)$$

in which:
- $R_7$, which may be identical or different, represent a monovalent hydrocarbon-based radical containing from 1 to 18 carbon atoms, and in particular a $C_1$-$C_{18}$ alkyl radical, a $O_2$-$C_{18}$ alkenyl radical or a ring containing 5 or 6 carbon atoms, for example methyl;
- $R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;
- $R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—$NHCOR_7$ radical;
- X– is an anion such as a halide ion, in particular chloride, or an organic acid salt (for example acetate);
- r represents a mean statistical value from 2 to 200 and in particular from 5 to 100;

These silicones are described, for example, in patent application EP-A 0 530 974.

e) amino silicones having formula (J):

$$H_2N-(C_mH_{2m})-NH-(C_nH_{2n})-Si\left[O-\underset{\underset{R_2}{|}}{\overset{\overset{R_1}{|}}{Si}}-O\right]_x\underset{\underset{R_3}{|}}{\overset{\overset{R_3}{|}}{Si}}-R_5\Bigg]_3 \quad (J)$$

in which:
- $R_1$, $R_2$, $R_3$ and $R_4$, which may be identical or different, denote a $C_1$-$C_4$ alkyl radical or a phenyl group;
- $R_5$ denotes a $C_1$-$C_4$ alkyl radical or a hydroxyl group;
- n is an integer ranging from 1 to 5;
- m is an integer ranging from 1 to 5;
and in which x is chosen such that the amine number is between 0.01 and 1 meq/g;

f) multiblockpolyoxyalkylenated amino silicones, of type (AB)n, A being a polysiloxane block and B being a polyoxyalkylenated block containing at least one amine group.

Said silicones are preferably constituted of repeating units having the following general formulae:

$$[-(SiMe_2O)_xSiMe_2-R-N(R'')-R'-O(C_2H_4O)_a(C_3H_6O)_b-R'-N(H)-R-]$$

or alternatively $$[-(SiMe_2O)_xSiMe_2-R-N(R'')-R'-O(C_2H_4O)_a(C_3H_6O)_b-]$$

in which:
- a is an integer greater than or equal to 1, preferably ranging from 5 to 200, more particularly ranging from 10 to 100;
- b is an integer comprised between 0 and 200, preferably ranging from 4 to 100, more particularly between from 5 and 30;
- x is an integer ranging from 1 to 10 000, more particularly from 10 to 5000;
- R" is a hydrogen atom or a methyl;
- R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —$CH_2CH_2CH_2OCH(OH)CH_2$— radical; preferentially R denotes a —$CH_2CH_2CH_2OCH(OH)CH_2$— radical;
- R', which may be identical or different, represent a divalent linear or branched $C_2$-$C_{12}$ hydrocarbon-based radical, optionally including one or more heteroatoms such as oxygen; preferably, R' denotes an ethylene radical, a linear or branched propylene radical, a linear or branched butylene radical, or a —$CH_2CH_2CH_2OCH(OH)CH_2$— radical; preferentially R' denotes —$CH(CH_3)$—$CH_2$—.

The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2.

The weight-average molecular weight (Mw) of the silicone is preferably comprised between 5000 and 1 000 000, more particularly between 10 000 and 200 000.

Mention may be made especially of the silicones sold under the names SilSoft™ A-843 or Silsoft™ A+ by Momentive.

g) the alkylamino silicones corresponding to formula (K) below:

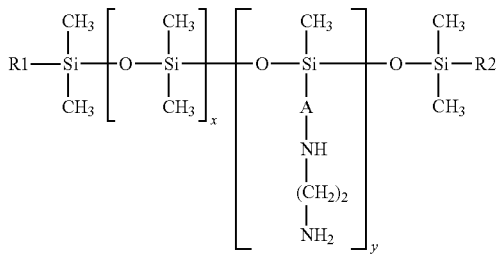

(K)

in which:
- x and y are numbers ranging from 1 to 5000; preferably, x ranges from 10 to 2000 and especially from 100 to 1000; preferably, y ranges from 1 to 100;
- $R_1$ and $R_2$, which may be identical or different, preferably identical, are linear or branched, saturated or unsaturated alkyl radicals, comprising 6 to 30 carbon atoms, preferably 8 to 24 carbon atoms and especially 12 to 20 carbon atoms;
- A denotes a linear or branched alkylene radical containing from 2 to 8 carbon atoms, Preferably, A comprises 3 to 6 carbon atoms, especially 4 carbon atoms; preferably, A is branched. Mention may be made especially of the following divalent radicals: —CH$_2$CH$_2$CH$_2$ and —CH$_2$CH(CH$_3$)CH$_2$—.

Preferably, $R_1$ and $R_2$, which may be identical or different, are saturated linear alkyl radicals comprising 6 to 30 carbon atoms, preferably 8 to 24 carbon atoms and especially 12 to 20 carbon atoms; mention may be made in particular of dodecyl, tetradecyl, pentadecyl, hexadecyl, heptadecyl, octadecyl, nonadecyl and eicosyl radicals; and preferentially, $R_1$ and $R_2$, which may be identical or different, are chosen from hexadecyl (cetyl) and octadecyl (stearyl) radicals.

Preferentially, the silicone is of formula (K) with:
- x ranging from 10 to 2000 and especially from 100 to 1000;
- y ranging from 1 to 100;
- A comprising 3 to 6 carbon atoms and especially 4 carbon atoms; preferably, A is branched; and more particularly A is chosen from the following divalent radicals: CH$_2$CH$_2$CH$_2$ and —CH$_2$CH(CH$_3$)CH$_2$—; and
- $R_1$ and $R_2$, which may be identical or different, being linear, saturated alkyl radicals comprising 6 to 30 carbon atoms, preferably 8 to 24 carbon atoms and especially 12 to 20 carbon atoms; chosen in particular from dodecyl, tetradecyl, pentadecyl, hexadecyl, heptadecyl, octadecyl, nonadecyl and eicosyl radicals; preferentially, $R_1$ and $R_2$, which may be identical or different, being chosen from hexadecyl (cetyl) and octadecyl (stearyl) radicals.

A preferred silicone of formula (K) is bis-cetearylamodimethicone (INCI name).

Mention may be made especially of the silicone sold under the name Silsoft™ AX by Momentive.

Preferably, the amino silicones according to the invention are chosen from the amino silicones of formula (F). A preferred silicone of formula (F) is amodimethicone (INCI name) sold under the tradename XIAMETER® MEM-8299 Cationic Emulsion by Dow Corning.

Non-Ionic Surfactants

Nonionic surfactants are compounds well known in themselves (see, e.g., in this regard, "Handbook of Surfactants" by M. R. Porter, Blackie & Son publishers (Glasgow and London), 1991, pp. 116-178), which is incorporated herein by reference in its entirety.

The nonionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned.

Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$) alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and a mixture thereof.

The nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

Examples of oxyalkylenated nonionic surfactants that may be mentioned include: oxyalkylenated ($C_8$-$C_{24}$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyalkylenated esters of saturated or unsaturated, linear or branched, $C_8$-$C_{30}$ acids and of sorbitol, saturated or unsaturated, oxyalkylenated plant oils, condensates of ethylene oxide and/or of propylene oxide, inter glia, alone or as mixtures.

The surfactants preferably contain a number of moles of ethylene oxide and/or of propylene oxide of between 2 and 100 and most preferably between 2 and 50.

In accordance with one preferred embodiment of the invention, the oxyalkylenated nonionic surfactants are chosen from oxyethylenated $C_8$-$C_{30}$ alcohols.

Examples of ethoxylated fatty alcohols (or $C_8$-$C_{30}$ alcohols) that may be mentioned include the adducts of ethylene oxide with lauryl alcohol, especially those containing from 9 to 50 oxyethylene groups and more particularly those containing from 10 to 25 oxyethylene groups (Laureth-10 to Laureth-25); the adducts of ethylene oxide with behenyl alcohol, especially those containing from 9 to 50 oxyethylene groups (Behenth-9 to Beheneth-50); the adducts of ethylene oxide with cetearyl alcohol (mixture of cetyl alcohol and stearyl alcohol), especially those containing from 10 to 30 oxyethylene groups (Ceteareth-10 to Ceteareth-30); the adducts of ethylene oxide with cetyl alcohol, especially those containing from 10 to 30 oxyethylene groups (Ceteth-10 to Ceteth-30); the adducts of ethylene oxide with stearyl alcohol, especially those containing from 10 to 30 oxyethylene groups (Steareth-10 to Steareth-30); the adducts of ethylene oxide with isostearyl alcohol, especially those containing from 10 to 50 oxyethylene groups (Isosteareth-10 to lsosteareth-50); and a mixture thereof.

As examples of polyglycerolated nonionic surfactants, polyglycerolated $C_8$-$C_{40}$ alcohols are preferably used.

In particular, the polyglycerolated $C_8$-$C_{40}$ alcohols correspond to the following formula:

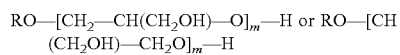

in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

According to one of the embodiments according to the present invention, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and a mixture thereof.

Examples of ethoxylated fatty esters that may be mentioned include the adducts of ethylene oxide with esters of lauric acid, palmitic acid, stearic acid or behenic acid, and a mixture thereof, especially those containing from 9 to 100 oxyethylene groups, such as PEG-9 to PEG-50 laurate; PEG-9 to PEG-50 palmitate; PEG-9 to PEG-50 stearate; PEG-9 to PEG-50 palmitostearate; PEG-9 to PEG-50 behenate; polyethylene glycol 100 EO monostearate; and a mixture thereof.

As glyceryl esters of fatty acids, glyceryl stearate (glyceryl mono-, di- and/or tristearate) (glyceryl stearate) or glyceryl ricinoleate and a mixture thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Croda, and a product containing glyceryl stearate (glyceryl mono- and distearate) and potassium stearate, can also be used.

The sorbitol esters of $C_8$-$C_{24}$ fatty acids and alkoxylated derivatives thereof can be selected from sorbitan palmitate, sorbitan trioleate and esters of fatty acids and alkoxylated sorbitan containing for example from 20 to 100 EO, such as for example polyethylene sorbitan trioleate (polysorbate 85) or the compounds marketed under the trade names Tween 20 or Tween 60 by Croda.

As esters of fatty acids and glucose or alkylglucose, in particular glucose palmitate, alkylglucose sesquistearates such as methylglucose sesquistearate, alkylglucose palmitates such as methylglucose or ethylglucose palmitate, methylglucoside fatty esters and more specifically the diester of methylglucoside and oleic acid (Methyl glucose dioleate), the mixed ester of methylglucoside and the mixture oleic acid/hydroxystearic acid (Methyl glucose dioleate/hydroxystearate), the ester of methylglucoside and isostearic acid (Methyl glucose isostearate), the ester of methylglucoside and lauric acid (Methyl glucose laurate), the mixture of monoester and diester of methylglucoside and isostearic acid (Methyl glucose sesqui-isostearate), the mixture of monoester and diester of methylglucoside and stearic acid (Methyl glucose sesquistearate) and in particular the product marketed under the name Glucate SS by Lubrizol, and a mixture thereof can be cited.

As ethoxylated ethers of fatty acids and glucose or alkylglucose, ethoxylated ethers of fatty acids and methylglucose, and in particular the polyethylene glycol ether of the diester of methylglucose and stearic acid with about 20 moles of ethylene oxide (PEG-20 methyl glucose distearate) such as the product marketed under the name GLUCAM E-20 DISTEARATE by Lubrizol, the polyethylene glycol ether of the mixture of monoester and diester of methylglucose and stearic acid with about 20 moles of ethylene oxide (PEG-20 methyl glucose sesquistearate) and in particular the product marketed under the name GLUCAMATE SSE-20 by Lubrizol, and a mixture thereof, can for example be cited.

As sucrose esters, saccharose palmito-stearate, saccharose stearate and saccharose monolaurate can for example be cited.

As sugar ethers, alkylpolyglucosides can be used, and for example decylglucoside such as the product marketed under the name MYDOL 10 by Kao Chemicals, the product marketed under the name PLATAREN 2000 by BASF, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by BASF, cocoglucoside such as the product marketed under the name PLANTACARE 818/UP by BASF, cetostearyl glucoside possibly mixed with cetostearyl alcohol, marketed for example under the name MONTANOV 68 by Seppic, under the name TEGO-CARE CG90 by Evonik, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, and a mixture thereof can in particular be cited.

Mixtures of glycerides of alkoxylated plant oils such as mixtures of ethoxylated (200 EO) palm and copra (7 EO) glycerides can also be cited.

It is preferable that the nonionic surfactant be selected from the group consisting of PEG-7 glyceryl cocoate, PEG-20 methylglucoside sesquistearate, PEG-20 glyceryl triisostearate, PG-5 dioleate, PG-4 diisostearate, PG-10 isostearate, PEG-8 isostearate, and PEG-60 hydrogenated castor oil.

Mixtures of these oxyethylenated derivatives of fatty alcohols and of fatty esters may also be used.

Preferably, the nonionic surfactant may be a nonionic surfactant with an HLB of 18.0 or less, such as from 4.0 to 18.0, more preferably from 6.0 to 15.0 and furthermore preferably from 9.0 to 13.0. The HLB is the ratio between the hydrophilic part and the lipophilic part in the molecule.

In some case, the nonionic surfactant is a fatty alkanolamide. Non-limiting examples of fatty alkanolamides that may be used include cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, and a mixture thereof.

Thickening Agents

The one or more thickening agents may be xanthan gum, guar gum, biosaccharide gum, cellulose, acacia Seneca gum, sclerotium gum, agarose, pechtin, gellan gum, hyaluronic acid. Additionally, the one or more thickeners may include polymeric thickeners selected from the group consisting of ammonium polyacryloyldimethyl taurate, ammonium acryloyldimethyltaurateNP copolymer, sodium polyacrylate, acrylates copolymers, polyacrylamide, carbomer, and acrylates/C10-30 alkyl acrylate crosspolymer. In some cases, the thickening agent includes ammonium polyacryloyldimethyl taurate and/or sodium polyacrylate.

Many thickening agents are water-soluble, and increase the viscosity of water or form an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water. Non-limiting examples of various types of thickeners include:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

b. Crosslinked Polyacrylate Polymers

The compositions of the present disclosure can optionally contain crosslinked polyacrylate polymers useful as thickeners or gelling agents including both cationic and nonionic polymers. Examples of useful crosslinked nonionic polyacrylate polymers and crosslinked cationic polyacrylate polymers are those described in U.S. Pat. Nos. 5,100,660, 4,849,484, 4,835,206, 4,628,078 U.S. Pat. No. 4,599,379 and EP 228,868, which are all incorporated herein by reference in their entirety.

c. Polyacrylamide Polymers

The compositions of the present disclosure can optionally contain polyacrylamide polymers, especially nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

d. Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™. CS11 from Michel Mercier Products Inc.

e. Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived form callus of plants belonging to *Polyantes* sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

Active Ingredients

The bi-phase micellar liquid products described herein may include one or more active ingredients. The products may include 10 ppm to 10 wt. % (100,000 ppm), 10 ppm to 5 wt. % (50,000 ppm), 10 ppm to 2.5 wt. % (25,000 ppm), 10 ppm to 1 wt. % (10,000 ppm), 10 ppm to 0.5 wt. % (5,000 ppm), 10 ppm to 0.1 wt. % (1,000 ppm), or 10 ppm to 500 ppm of one or more active ingredients. In some cases, the one or more active ingredients is present in an amount from 10, 20, 30, 40, 50, 60, 70, 80, 90, 100, 150, or 200 ppm to 500, 600, 700, 800, 900, 0.1 wt. % (1000 ppm), 0.5 wt. % (5,000 ppm), 1 wt. % (10,000 ppm)), 5 wt. % (50,000 ppm), or 10 wt. % (100,000 ppm).

Non-limiting examples of the one or more active agents include adenosine, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, and a coenzyme. In some cases the active ingredient is adenosine.

In one embodiment the bi-phase micellar liquid product comprises an active ingredient such as a humectant and moisturizing ingredients, an anti-aging agent, a depigmenting agent, an anti-wrinkle agent, or an agent that treats oily skin.

Humectants and moisturizing ingredients may be in particular glycerol and its derivatives, urea and its derivatives, especially Hydrovance marketed by National Starch, lactic acid, hyaluronic acid, AHA, BHA, sodium pidolate, xylitol, serine, sodium lactate, ectoin and its derivatives, chitosan and its derivatives, collagen, plankton, an extract of Imperata cylindra sold under the name Moist 24 by Sederma, homopolymers of acrylic acid as Lipidure-HM of NOF Corporation, beta-glucan and in particular sodium carboxymethyl beta-glucan Mibelle-AG-Biochemistry, a mixture of oils passionflower, apricot, corn, and rice bran sold by Nestle under the name NutraLipids, a C-glycoside derivatives, in particular the C-13-D-xylopyranoside-2-hydroxypropane in the form of a solution at 30% by weight of active material in a water/propylene glycol mixture (60/40 wt %) as the product produced by the company Chimex under the trade name "Mexoryl SBB", a rose hip oil marketed by Nestle, a micro-algae extract Prophyridium cruentum enriched with zinc, marketed under the name by Vincience Algualane Zinc spheres of collagen and chondroitin sulfate of marine origin (Atelocollagen) sold by the company Engelhard Lyon under the name Marine Filling Spheres, hyaluronic acid spheres such as those marketed by Engelhard Lyon, and arginine.

Depigmenting agents include vitamin C and its derivatives and especially vitamin CG, CP and 3-O ethyl vitamin C, alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, ceramides and their counterparts, derived from plants such as chamomile, bearberry, the aloe family (vera, ferox, bardensis), mulberry, skullcap, a water kiwi fruit (*Actinidia chinensis*) marketed by Gattefosse, an extract of *Paeonia suffruticosa* root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Particular depigmenting agents include vitamin C and its derivatives and especially vitamin CG, CP and 3-O ethyl vitamin C, alpha and beta arbutin, ferulic acid, kojic acid, resorcinol and derivatives, D pantheteine calcium sulfonate, lipoic acid, ellagic acid, vitamin B3, a water kiwi fruit (*Actinidia chinensis*) marketed by Gattefosse, an extract of *Paeonia suffruticosa* root, such as that sold by the company Ichimaru Pharcos under the name Botanpi Liquid B.

The term "anti-wrinkle active" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Exemplary anti-wrinkle actives may be chosen from: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof.

Examples of such compounds are: adenosine and its derivatives and retinol and its derivatives such as retinol palmitate, ascorbic acid and its derivatives such as magnesium ascorbyl phosphate and ascorbyl glucoside; tocopherol and derivatives thereof such as tocopheryl acetate, nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxy-propane as described in particular in EP-1345919, plant extracts including sea fennel and extracts of olive leaves, as well as plant and hydrolysates thereof such as rice protein hydrolysates or soybean proteins; algal extracts and in particular *laminaria*, bacterial extracts, the sapogenins such as diosgenin and extracts of *Dioscorea* plants, in particular wild yam, comprising: the α-hydroxy acids, β-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and mixtures thereof.

As adenosine derivatives include especially non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside.

Other derivatives include adenosine receptor agonists such as adenosine adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N 6-phenethyladenosine, 2-p-(2-carboxy-ethyl) phenethyl-amino-5'-N-ethylcarboxamido adenosine (CGS-21680), N-ethylcarboxamido-adenosine (NECA), the 5'(N-cyclopropyl)-carboxamidoadenosine, DPMA (PD 129.944) and metrifudil.

In one embodiment the bi-phase micellar liquid product comprises an active ingredient that addresses oily skin. These actives can be sebo-regulating or antiseborrhoeic agents capable of regulating the activity of sebaceous glands. These include: retinoic acid, benzoyl peroxide, sulfur, vitamin B6 (pyridoxine or) chloride, selenium, samphire—the cinnamon extract blends, tea and octanoylglycine such as—15 Sepicontrol A5 TEA from Seppic—the mixture of cinnamon, sarcosine and octanoylglycine marketed especially by Seppic under the trade name Sepicontrol A5—zinc salts such as zinc gluconate, zinc pyrrolidonecarboxylate (or zinc pidolate), zinc lactate, zinc aspartate, zinc carboxylate, zinc salicylate 20, zinc cysteate;—derivatives particularly copper and copper pidolate as Cuivridone Solabia—extracts from plants of *Arnica montana, Cinchona succirubra, Eugenia caryophyllata, Humulus lupulus, Hypericum perforatum, Mentha pipenta* 25 *Rosmarinus officinalis, Salvia officinalis* and *Thymus vulgaris*, all marketed for example by Maruzen—extracts of meadowsweet (*Spiraea ulmaria*), such as that sold under the name Sebonormine by Silab—extracts of the alga *Laminaria saccharina*, such as that sold under the 30 name Phlorogine by Biotechmarine—the root extracts of burnet mixtures (*Sanguisorba officinalis/Poterium officinale*), rhizomes of ginger (*Zingiber officinalis*) and cinnamon bark (*Cinnamomum cassia*), such as that sold under the name Sebustop by Solabia—extracts of flaxseed such as that sold under the name Linumine by Lucas Meyer—Phellodendron extracts such as those sold under the name Phellodendron extract BG by Maruzen or Oubaku liquid B by Ichimaru Pharcos—of argan oil mixtures extract of *Serenoa serrulata* (saw palmetto) extract and sesame seeds such as that sold under the name Regu SEB by Pentapharm—mixtures of extracts of willowherb, of Terminalia chebula, nasturtium and of bioavailable zinc (microalgae), such as that sold under the name Seborilys Green Tech;—extracts of Pygeum afrianum such as that sold under the name Pygeum afrianum sterolic lipid extract by Euromed—extracts of *Serenoa serrulata* such as those sold under the name Viapure Sabal by Actives International, and those sold by the company Euromed—of extracts of plantain blends, *Berberis aquifolium* and sodium salicylate 20 such as that sold under the name Seboclear Rahn—extract of clove as that sold under the name Clove extract powder by Maruzen—argan oil such as that sold under the name Lipofructyl Laboratories Serobiologiques; 25—lactic protein filtrates, such as that sold under the name Normaseb by Sederma—the seaweed *laminaria* extracts, such as that sold under the name Laminarghane by Biotechmarine—oligosaccharides seaweed *Laminaria digitata*, such as that sold under the name Phycosaccharide 30 AC by the company Codif—extracts of sugar cane such as that sold under the name Policosanol by the company Sabinsa, the sulfonated shale oil, such as that sold under the name lchtyol Pale by lchthyol—extracts of 'meadowsweet (*Spiraea ulmaria*) such as that sold under the name Cytobiol Ulmaire by societeLibiol—sebacic acid, especially sold in the form of a sodium polyacrylate gel under the name Sebosoft by Sederma—glucomannans extracted from konjac tuber and modified with alkylsulfonate chains such as that sold under the name Biopol Beta by Arch Chemical—extracts of *Sophora angustifolia*, such as those sold under the name Sophora powder or Sophora extract by Bioland—extracts of *cinchona* bark succirubra such as that sold under the name Red Bark HS by Alban Muller—extracts of *Quillaja saponaria* such as that sold under the name 15 Panama wood HS by Alban Muller—glycine grafted onto an undecylenic chain, such as that sold under the name Lipacide UG OR by SEPPIC—the mixture of oleanolic acid and nordihydroguaiaretic acid, such as that sold under the form of a gel under the name AC.Net by Sederma; 20—phthalimidoperoxy-hexanoic acid—citrate tri (C12-C13) sold under the name COSMACOL® ECI by Sasol; trialkyl citrate (C14-C15) sold under the name COSMACOL® ECL by Sasol—10-hydroxydecanoic acid, including mixtures acid-hydroxydecanoic October 25, sebacic acid and 1,10-decandiol such as that sold under the name Acnacidol BG by Vincience and mixtures thereof.

Implementation of the present disclosure is provided by way of the following examples. The examples serve to illustrate the technology without being limiting in nature.

Example 1

Bi-Phase Micellar Liquid Product

| BI-PHASE MICELLAR LIQUID PRODUCT | | |
|---|---|---|
| COMPONENT | US INCI NAME | AMOUNT (WT. %) |
| Fatty Phase — Fatty Compound | ISOHEXADECANE | 6 |
| Silicone | CYCLOPENTASILOXANE | 9 |
| Aqueous Phase — Active (Ceramides) | CERAMIDE EOP | ≤0.5 |
| | CERAMIDE NP | |
| | CERAMIDE AP | |
| Active | CHOLESTEROL | ≤0.1 |
| Active | PHYTOSPHINGOSINE | ≤0.1 |
| Nonionic Surfactants | POLYGLYCERYL-4 CAPRATE | 0.3 |
| | DECYL GLUCOSIDE | |
| Water-Soluble Solvents | HEXYLENE GLYCOL | 5.4 |
| | GLYCERIN | |
| | ETHYLHEXYLGLYCERIN | |
| Salt | SODIUM CHLORIDE | 0.4 |
| pH Adjusting Agent/Buffering Agent | DIPOTASSIUM PHOSPHATE | 1 |
| | POTASSIUM PHOSPHATE | |
| Chelating Agent | DISODIUM EDTA | ≤1 |
| Preservatives | MYRTRIMONIUM BROMIDE | |
| | PHENOXYETHANOL | |
| Water | WATER | ~77 |

Example 2

Improving Skin Hydration

A clinical study was carried out to evaluate the bi-phase micellar product of Example 1. The study investigated the effectiveness of the product in improving skin hydration and repairing/enhancing skin barrier function. A total of twenty-seven (26) female subjects consented, enrolled, and completed the study.

Changes in skin conductance, impedance or capacitance are used to study epidermal hydration in vivo. Measurements are made to determine the difference in dielectric constant between the skin and water; skin has a low dielectric constant and water has a high dielectric constant of 81. When skin is hydrated, conductance and capacitance increases and impedance decreases. The measuring capacitor shows changes in capacitance according to the moisture content of the tissue.

Corneometer CM 825 (Courage and Khazaka, Germany) was used to measure the electrical capacitance/hydration of the skin. Three replicate measurements were taken from randomized sites that had been treated with the product of Example 1 and control sites (untreated skin) at each measurement interval. If one measurement was more than ±10 units from the other measurements this measurement was not included in the analysis.

Three days prior to the start of the study, enrolled subjects began the washout period. Subject received a neutral soap bar to use for cleansing their volar forearms (i.e., bathing) for the washout period. Subject were given specific instructions prohibiting the use of all personal care products (e.g., lotions, creams), on the test site (volar forearms) for the entire washout and study duration.

Following the washout period, subjects returned to the testing facility for baseline measurements. The volar surface of the forearms were gently wiped with a damp disposable washcloth and patted dry with a paper towel. Treatment sites and control sites (untreated) were randomly assigned using a computer generated randomization code.

To determine baseline (pre-treatment), skin hydration readings were taken by Corneometer. Following baseline measurements, application of the product of Example 1 on the designated treatment sites was performed. After application, subjects remained in the exam room and were instructed to keep their volar forearms uncovered and exposed. At predetermined times, skin hydration readings were taken by Corneometer. At 8 and 24 hours post-treatment, TEWL readings were taken. Subjects were dismissed after the 8 hour measurements were obtained but were instructed not to wet (e.g., no shower, bathing, or swimming) or apply products to their volar forearms until after the 24 hour measurements were obtained. Approximately 24 hours (±30 min) after product application to the test sites, subjects returned for final TEWL measurements. The results are reported in Table 1 below.

TABLE 1

(Skin Hydration)

| Assessment | Time Point | Site | N | Mean % Change from BL | p-value (from BL) | p-value (Mean Change Treated vs. Untreated) |
|---|---|---|---|---|---|---|
| Hydration | Baseline | Treated | 26 | | | |
| | | Untreated | 26 | | | |
| | 8 Hours | Treated | 26 | 18.16% | ≤0.001 | ≤ 0.001 |
| | | Untreated | 26 | 0.79% | 0.065 | |
| | 24 Hours | Treated | 26 | 9.33% | ≤0.001 | ≤ 0.001 |
| | | Untreated | 26 | 0.62% | 0.418 | |

*Bold indicates statistical significance p ≤ 0.05; positive mean percent change values indicate an improvement At baseline there was no statistical difference in the skin hydration values for the treated and untreated sites. However, at 8 hours and 24 hours post application, there was a statistically significant increase (improvement) in skin hydration values for the sites treated with the product of Example 1 compared to baseline. Additionally, at 8 hours and 24 hours post application, there was a statistically significant difference in skin hydration values between the treated and the untreated sites.

Example 3

Improving Skin Barrier Function

A clinical study was carried out to evaluate the bi-phase micellar product of Example 1. The study investigated the effectiveness of the product in repairing/enhancing skin barrier function. A total of twenty-seven (30) female subjects consented, enrolled, and completed the study.

Transepidermal water loss (TEWL) is a measure of skin barrier function. It measures the amount of water that passes from inside the body through the epidermis (the epidermal layer of the skin) to the surrounding atmosphere via diffusion and evaporation. An evaporimeter probe is used, which includes two sensors that measure the vapor pressure gradient arising within the device's chamber and between the skin and the surrounding air. TEWL measurements were determined using DermaLab Evaporimeter (Cortex Technology, Hadsun, Denmark). Decreases in TEWL values indicate an improvement in skin barrier function, such that less water is lost through the skin barrier. TEWL measurements were taken from the randomized designated sites treated with the product of example 1 and the control sites (untreated skin) at 1 hour post treatment.

Three days prior to the start of the study, enrolled subjects began the washout period. Subject received a neutral soap bar to use for cleansing their volar forearms (i.e., bathing) for the washout period. Subject were given specific instructions prohibiting the use of all personal care products (e.g., lotions, creams), on the test site (volar forearms) for the entire washout and study duration. Following the washout period, subjects returned to the testing facility for baseline measurements. The volar surface of the forearms were gently wiped with a damp disposable washcloth and patted dry with a paper towel. Treatment sites and control sites (untreated) were randomly assigned using a computer generated randomization code.

TEWL readings by Evaporimeter were taken at the designated sites (treated and untreated). Packing tape was applied to the designated sites. The tape was then stripped from the sites. TEWL readings by Evaporimeter were performed and repeated taping and stripping carried out until a TWEL measurement greater than 20 $g/m^2h$ was reached.

Following baseline measurements (post tape stripping), application of the product of Example 1 on the designated sites was performed. After application, subjects remained in the exam room and were instructed to keep their volar forearms uncovered and exposed. At 1 hours post-treatment TEWL measurements were recorded. The results are reported in Table 2 below.

TABLE 2

(Skin Barrier Function)

| Assessment | Time Point | Site | N | Mean % Change from BL | p-value (from BL) | p-value (Mean Change Treated vs. Untreated) |
|---|---|---|---|---|---|---|
| TEWL | Baseline | Treated | 30 | | | |
| | | Untreated | 30 | | | |
| | 1 Hours | Treated | 30 | −32.28% | ≤0.001 | ≤ 0.001 |
| | | Untreated | 30 | −5.12% | 0.537 | |

*Bold indicates statistical significance p ≤ 0.05; positive mean percent change values indicate an improvement At baseline there was no statistical difference in the TEWL values for the treated and untreated sites. However, at 1 hour post application, there was a statistically significant decrease (improvement) in TEWL values for the sites treated with the product of Example 1 compared to baseline. Additionally, at 1 hour post application, there was a statistically significant difference in TEWL values between the treated and the untreated sites.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" (or "comprise," "have," and "include") are used in their open, non-limiting sense.

The terms "a," "an," and "the" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

The term "transparent" or "clear" means that the composition/product allows light to pass through so that objects behind can be seen. A transparent material allows light to pass through, and makes it possible to distinguish alphanumeric characters using 5 mm thick samples. A simple example of a transparent material is a glass window. One can see through a glass window. More specifically, term "transparent" relates to a material having a maximum light transmittance value, at a wavelength equal to 500 nm, through a sample 1 cm thick, of at least 60% and preferably of at least 70%.

The term "opaque" or "cloudy" means that the composition/product that is not transparent. Steam on a window is an example of an opaque or cloudy scenario.

Other than in the operating examples, or where otherwise indicated, all numbers expressing quantities of ingredients and/or reaction conditions can be modified in all instances by the term "about," meaning within +/−5% of the indicated number.

Some of the various categories of components identified for the hair-treatment compositions may overlap. In such cases where overlap may exist and the composition/product includes both components (or more than two overlapping components), an overlapping compound does not represent more than one component. For example, a fatty acid may be defined as both a "fatty compound" and a "surfactant/emulsifier." If a particular composition/product includes both a fatty compound component and an emulsifier component, a single fatty acid can serve as only a fatty compound or a surfactant/emulsifier (a single fatty acid does not serve as both the fatty compound and the surfactant/emulsifier).

All percentages, parts and ratios herein are based upon the total weight of the compositions of the present invention, unless otherwise indicated.

"Keratinous substrates" as used herein, includes, but is not limited to keratin fibers such as skin, hair, and scalp on the human head.

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term "treat," and its grammatical variations, relates to contacting hair with the hair-treatment compositions of the present disclosure.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 5% by weight of a specific material added to a composition, based on the total weight of the compositions. Nonetheless, the compositions may include less than about 3 wt. %, less than about 2 wt. %, less than about 1 wt. %, less than about 0.5 wt. %, less than about 0.1 wt. %, or none of the specified material.

The term "essentially anhydrous" or "substantially anhydrous" as used herein, for example, in the context of an "essentially anhydrous hair-treatment composition" or a "substantially anhydrous hair-treatment composition" means that the composition includes less than about 5% by weight of water. Nonetheless, the composition may include less than about 4 wt. %, less than about 3 wt. %, less than about 2 wt. %, less than about 1 wt. %, less than about 0.5 wt. %, less than about 0.1 wt. % of water, less than about 0.05 wt. % water, or less than 0.01 wt. % water.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A bi-phase micellar liquid product comprising:
   (a) about 5 to about 40 wt. % of a fatty phase, the fatty phase comprising:
      one or more fatty compounds;
      one or more silicones; and
   (b) about 60 to about 95 wt. % of an aqueous phase, the aqueous phase comprising:
      micelles suspended in the aqueous phase (b), wherein the micelles comprise one or more ceramides;
      one or more water-soluble solvents;
      one or more surfactants; and
      water,
      wherein the fatty phase (a) and the aqueous phase (b) are separated by a single interface disposed between the fatty phase (a) and the aqueous phase (b).

2. A product of claim 1, wherein the micelles suspended in the aqueous phase (b) further comprise cholesterol and phytosphingosine.

3. A product of claim 2, comprising greater than zero to about 1 wt. % of the cholesterol, based on the total weight of the product; and greater than zero to about 1 wt. % of the phytosphingosine, based on the total weight of the product.

4. A product of claim 1 comprising about 1 to about 35 wt. % of the one or more fatty compounds, based on the total weight of the product.

5. A product of claim 1 comprising about 1 to about 35 wt. % of the one or more silicones, based on the total weight of the product.

6. A product of claim 1 comprising greater than zero to about 1 wt. % of the one or more ceramides, based on the total weight of the product.

7. A product of claim 1 comprising about 1 to about 40 wt. % of the one or more water-soluble solvents, based on the total weight of the product.

8. A product of claim 1 comprising about 0.01 to about 5 wt. % of the one or more surfactants, based on the total weight of the product.

9. A product of claim 1, wherein the one or more surfactants comprises one or more nonionic surfactants.

10. A product of claim 9, wherein the one or more nonionic surfactants are selected from the group consisting of polyglycerol esters, alkylpolyglucosides, alkyl(ether) phosphates, fatty acid alkanolamides, and a mixture thereof.

11. A product of claim 10, wherein the one or more nonionic surfactant are selected from the group consisting of polyglycerol esters, alkylpolyglucosides, and a mixture thereof.

12. A product of claim 9 comprising about 0.01 to about 5 wt. % of the one or more nonionic surfactants.

13. A product of claim 1, wherein the aqueous phase further comprises one or more preservatives.

14. A product of claim 13, wherein the one or more preservatives are selected from the group consisting para-hydroxybenzoic acid esters, phenoxyethanol, imidazolidinyl urea, diazolidinyl urea, chlorhexidine digluconate, sodium benzoate, caprylyl glycol, iodopropynyl butyl carbamate, pentylene glycol, alkyl trimethylammonium bromides, dodecyl-trimethylammonium bromide, hexadecyltrimethyl-ammonium bromide, and a mixture thereof.

15. A product of claim 13 comprising greater than zero to about 5 wt. % of the one or more preservatives, based on the total weight of the product.

16. A product of claim 1 comprising about 50 to about 90 wt. % of the water.

17. A product of claim 1, wherein the one or more fatty compounds are selected from the group consisting of oils, waxes, alkanes, fatty alcohols, fatty acids, fatty alcohol derivatives, fatty acid derivatives esters of fatty alcohols, hydroxy-substituted fatty acids, waxes, triglyceride compounds, lanolin, ceramide, and a mixture thereof.

18. A product of claim 1, wherein the one or more silicones are selected from the group consisting of polyorganosiloxanes, polyalkylsiloxanes, polyarylsiloxanes, polyalkarylsiloxanes, polyestersiloxanes, and a mixture thereof.

19. A product of claim 18, wherein the one or more silicones are selected from the group consisting of dimethicone, cyclomethicone (cyclopentasiloxane), amodimethicone, trimethyl silyl amodimethicone, phenyl trimethicone, trimethyl siloxy silicate, and a mixture thereof.

20. A product of claim 1, wherein the one or more ceramides are selected from a group consisting of ceramide-EOS, ceramide-NS, ceramide-NP, ceramide-EOH, ceramide-AS, ceramide-NH, ceramide-AP, ceramide-AH, Ceramide-OS, ceramide-OH, and a mixture thereof.

21. A product of claim 20 comprising three or more ceramides.

22. A product of claim 1, wherein the one or more water-soluble solvents are selected from the group consisting of glycerin, $C_{1-4}$ alcohols, organic solvents, polyols, glycols, and a mixture thereof.

23. A method for cleansing the skin comprising applying a product of claim 1 to the skin and removing at least a portion of the product from the skin.

24. A method for hydrating the skin comprising applying a product of claim 1 to the skin.

25. A product of claim 2, wherein both the fatty phase and the aqueous phase are transparent when separated from each other.

* * * * *